US010408741B2

(12) United States Patent
Hwang et al.

(10) Patent No.: US 10,408,741 B2
(45) Date of Patent: Sep. 10, 2019

(54) OPTICAL PHANTOM FOR PRODUCING A TIME-RESOLVED DIFFUSE REFLECTANCE SPECTRUM

(71) Applicant: The United States of America, as represented by the Secretary of Commerce, Washington, DC (US)

(72) Inventors: Jeeseong C. Hwang, Louisville, CO (US); Heidrun Wabnitz, Blankenfelde-Mahlow (DE)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 0 days.

(21) Appl. No.: 15/994,431

(22) Filed: May 31, 2018

(65) Prior Publication Data
US 2018/0348119 A1    Dec. 6, 2018

(30) Foreign Application Priority Data
May 31, 2017    (DE) .................. 10 2017 111 957

(51) Int. Cl.
| G01N 21/25 | (2006.01) |
| G01N 21/27 | (2006.01) |
| G01N 33/49 | (2006.01) |
| A61B 5/1455 | (2006.01) |
| A61B 5/00 | (2006.01) |
| A61B 5/1495 | (2006.01) |

(52) U.S. Cl.
CPC ......... *G01N 21/255* (2013.01); *A61B 5/1495* (2013.01); *A61B 5/14553* (2013.01); *A61B 5/7246* (2013.01); *G01N 21/27* (2013.01); *G01N 33/4925* (2013.01); *G01N 2201/0675* (2013.01); *G01N 2201/0683* (2013.01); *G01N 2201/0893* (2013.01)

(58) Field of Classification Search
CPC .. G01N 21/255; A61B 5/14553; A61B 5/1495
USPC ........................................ 356/300
See application file for complete search history.

(56) References Cited

U.S. PATENT DOCUMENTS

| 5,274,385 A | 12/1993 | Riza |
| 8,571,418 B2 | 10/2013 | Wada et al. |
| 2008/0089698 A1* | 4/2008 | Jiang .................. H04B 10/505 398/189 |

OTHER PUBLICATIONS

Wabnitz, H., et al., "Time-resolved imaging in diffusive media", Optical Biomedical Diagnostics, 2016.
Ferrari, M., et al., "Near infrared brain and muscle oximetry: from the discovery to current applications", Journal of Near Infrared Spectroscopy, 2012, vol. 20.
(Continued)

*Primary Examiner* — Roy M Punnoose
(74) *Attorney, Agent, or Firm* — Office of Chief Counsel for National Institute of Standards and Technology

(57) ABSTRACT

An optical phantom produces a time-resolved diffuse reflectance spectrum and includes: a light source; a spatial light modulator; and an optical delay line including optical fibers of different length that produce different time-of-flight distributions, such that different time-of-flight distributions are combined and produce phantom light having the time-resolved diffuse reflectance spectrum.

17 Claims, 16 Drawing Sheets

(56) References Cited

OTHER PUBLICATIONS

Fujisaka, T., et al., "A Clinical Tissue Oximeter Using NIR Time-Resolved Spectroscopy", Adv. Exp. Med. Biol., 2016, 427-433, vol. 876.

Pifferi, A., et al., "New frontiers in time-domain diffuse optics, a review", Journal of Biomed. Opt., 2016, 91310, vol. 21.

Bickler, P.E., et al., "Factors affecting the performance of 5 cerebral oximeters during hypoxia in healthy volunteers", Anesthesia-Analgesia, 2013, 813-823, vol. 117.

Hyttel-Sorensen, S., et al., "Calibration of a prototype NIRS oximeter against two commercial devices on a blood-lipid phantom", Biomedical Optics Express, 2013, 1662-1672, vol. 4 No. 9.

Kleiser. S., et al., "Comparison of tissue oximeters on a liquid phantom with adjustable optical properties", Biomedical Optics Express, 2016, 2973-2992, vol. 7 No. 8.

Martelli, F., et al., "Optimal estimation reconstriction of the optical properties of a two-layered tissue phantom from time-resolved single-distance measurements", Journal of Biomedical Optics, 2015, 115001, vol. 20.

Spinelli, L., et al., "Determination of reference values for optical properties of liquid phantoms based on Intralipid and India ink", 2014, Biomedical Optics Express, 2037-2053, vol. 5.

Hornberger, C., et al., "A prototype device for standardized calibration of pulse oximeters", 2000, 161-169, vol. 16.

Chon, B., et al., "Digital phantom generated by spectral and spatial light modulators", Journal of Biomedical Optics, 2015, 121309, vol. 20.

Wabnitz, H., et al., "Tissue oximeter validation: Digital phantom approach—Concept", Presentation at ISO TC "Oximeter", 2016.

Selb, J., et al., "Comparison of a layered slab and an atlas head model for Monte Carlo fitting of time-domain near-infrared spectroscopy data of the adult head", Journal of Biomedical Optics, 2014, 16010, vol. 19.

Steinkellner, O., et al., "Optical bedside monitoring of cerebral perfusion: technological and methodological advances applied in a study on acute ischemic stroke", Journal of Biomedical Optics, 2010, 061708, vol. 15 No. 6.

Selb, J., et al., "Time-gated optical system for depth-resolved functional brain imaging", Journal of Biomedical Optics, 2006, 044008, vol. 11.

Boulder Nonlinear Systems (BNS), Internet Publication, retrieved on May 17, 2018, URL: http://bnonlinear.com/research-development/beam-pulse-shaping.

Weiner, A.M., "Ultrafast optical pulse shaping: A tutorial review", Optics Communications, 2011, 3669-3692, vol. 284.

* cited by examiner

OPTICAL PHANTOM FOR PRODUCING A TIME-RESOLVED DIFFUSE REFLECTANCE SPECTRUM

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, Md., 20899; voice (301) 301-975-2573; email tpo@nist.gov.

CROSS REFERENCE TO RELATED APPLICATIONS

This application claims priority to German Patent Application, Serial No. 10 2017 111 957.4, filed May 31, 2017, the disclosure of which is incorporated herein by reference in its entirety.

BRIEF DESCRIPTION

Disclosed is an optical phantom to produce a time-resolved diffuse reflectance spectrum, the optical phantom comprising: a light source that produces a first light; a spatial light modulator comprising a plurality of mirrors arranged in an array, the mirrors being independently controlled to reflect the first light in a plurality of light paths comprising a first light path and a second light path, such that the spatial light modulator: receives the first light over the plurality of mirrors; selectively reflects the first light as filtered light into the light paths such that the first light path includes a first photon flux and the second light path includes a second photon flux, the first photon flux being greater than the second photon flux; and an optical delay line comprising a plurality of optical fibers that comprises a first delay fiber and a second delay fiber, such that: a first optical entrance of the first delay fiber is disposed in the first light path and receives the first photon flux from the spatial light modulator; a second optical entrance of the second delay fiber is disposed in the second light path and receives the second photon flux from the spatial light modulator; the first delay fiber has a first length and produces a first time-of-flight distribution of the first photon flux after propagating through the first delay fiber; and the second delay fiber has a second length and produces a second time-of-flight distribution of the second photon flux after propagating in the second delay fiber; the first length being different than the second length so that the first time-of-flight distribution is different than the second time-of-flight distribution; and a combination of the first time-of-flight distribution and the second time-of-flight distribution are combined to produce phantom light having the time-resolved diffuse reflectance spectrum.

Also disclosed is an optical phantom for testing a measuring device for time-resolved diffuse optical spectroscopy, the optical phantom comprising: an input optic in optical communication with a light supply line; a filter device in optical communication with the light supply line and disposed in a direction of propagation of light from light supply line; and an optical delay line in optical communication with the filter device and comprising a plurality of optical fibers, the optical delay fibers being arranged relative to the filter device such that light received by each of optical delay fiber is individually filtered by the filter device, the optical delay fibers being joined to receive light leaving the filter device, such that the optical delay line produces phantom light with time-resolved diffuse reflectance spectrum in response to receiving first light with an initial time-of-flight distribution at input optic, wherein optical delay fibers comprise different optical path lengths for light such that output pulse lengths of photon time-of-flight distributions from the optical delay fibers are greater than an input pulse length of the first light, and the combination of the optical delay line and the filter device provide the time-resolved diffuse reflectance spectrum that mimics a photon time-of-flight distribution produced by biological tissue upon subjecting the biological tissue to a pulse of light from the measuring device.

Also disclosed is a method for producing phantom light having a time-resolved diffuse reflectance spectrum for testing a measuring device for time-resolved diffuse optical spectroscopy of biological tissue, the method comprising: illuminating a filter device with an input light pulse from an input optic, wherein each filter element of the filter device receives photons as a partial light pulse from the input light pulse incident on the filter device; filtering the partial light pulses by the filter device, a filter transmission varies for at least one of the partial light pulses; guiding of the partial light pulses along optical paths wi of varying lengths of an optical delay line; and merging the partial light pulses by a light collector arranged in optical communication with the filter device in a direction of light propagation, such that output photons exit an output surface of the light collector, wherein the optical paths wi are selected and filtering is conducted such that a time-resolved diffuse reflectance spectrum of phantom light mimics a photon time-of-flight distribution produced from subjecting a biological tissue to probe light.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that an optical phantom herein provides a waveform synthesizer that generates a controlled waveform with picosecond (ps) time resolution and a time-resolved diffuse reflectance spectrum that mimics light entering, propagating through, and exiting biological tissue. In a light-diffusing material such as biological tissue, a photon time-of-flight distribution (TOFD) have a property that includes temporal broadening and intensity attenuation for a transmitted light pulse associated with tissue optical properties such as scattering and absorption. The optical phantom produces a waveform that mimics TOFDs for a physiological condition of a tissue such as blood oxygenation in cerebral tissue such that the optical phantom provides a cerebral tissue oximetry standard. Surprisingly and advantageously, the optical phantom provides selective tailoring of an arbitrary shape of a light pulse.

Figure 9:
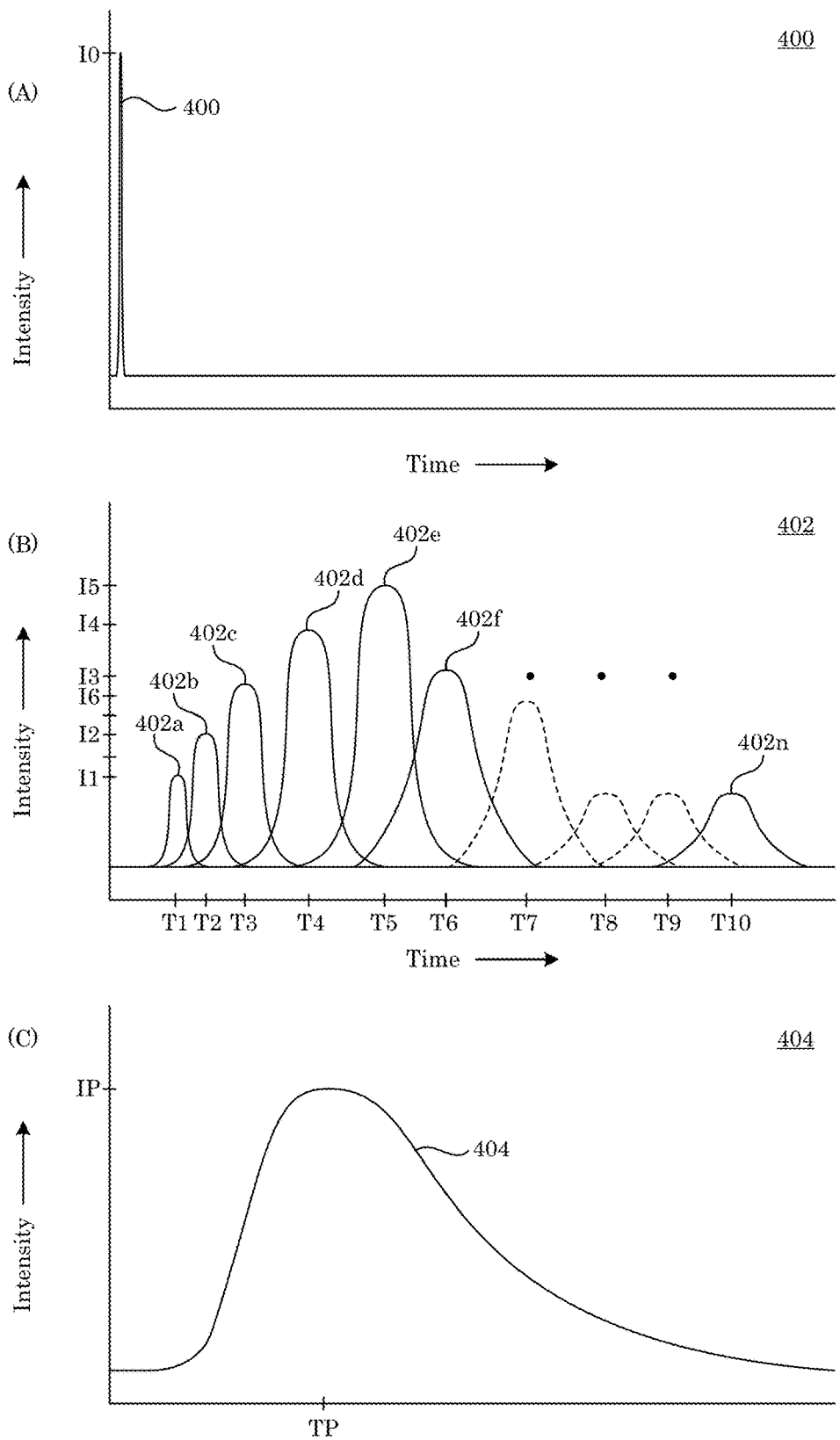
FIG. 9 shows an initial time-of-flight distribution (TOFD) in panel A, a plurality of delayed TOFDs in panel B, and a phantom TOFD in panel C.

In an embodiment, with reference to FIG. 1, FIG. 2, FIG. 3, FIG. 4, FIG. 5, FIG. 6, and FIG. 7, optical phantom 200 produces a time-resolved diffuse reflectance spectrum 404 and includes: light source 210 that produces first light 212; a filter device such as spatial light modulator 214 that includes a plurality of filter elements such as mirrors 216 arranged in array 218, mirrors 216 being independently controlled to reflect first light 212 in a plurality of light paths 220 including first light path 222 and second light path 224, such that spatial light modulator 214: receives first light 212 over the plurality of mirrors 216; selectively reflects first light 212 as filtered light 242 into light paths 220 such that first light path 222 includes first photon flux 226 and second light path 224 includes second photon flux 228, first photon flux 226 being greater than second photon flux 228; and optical delay line 230 including a plurality of optical fibers 232 that includes first delay fiber 234 and second delay fiber 236, such that: first optical entrance 238 of first delay fiber 234 is disposed in first light path 222 and receives first photon flux 226 from spatial light modulator 214; second optical entrance 240 of second delay fiber 236 is disposed in second light path 224 and receives second photon flux 228 from spatial light modulator 214; first delay fiber 234 has first length L1 and produces first time-of-flight distribution (e.g., 402a shown in panel B of FIG. 9) of first photon flux 226 after propagating through first delay fiber 234; and second delay fiber 236 has second length L2 and produces second time-of-flight distribution (e.g., 402b as shown in panel B of FIG. 9) of second photon flux 228 after propagating in second delay fiber 236; first length L1 being different than second length L2 so that first time-of-flight distribution 402a is different than second time-of-flight distribution 402b; and a combination of first time-of-flight distribution 402a and second time-of-flight distribution 402b are combined to produce phantom light 244 having a combined TOFD referred to as time-resolved diffuse reflectance spectrum 404 shown in panel C of FIG. 9.

Figure 2:
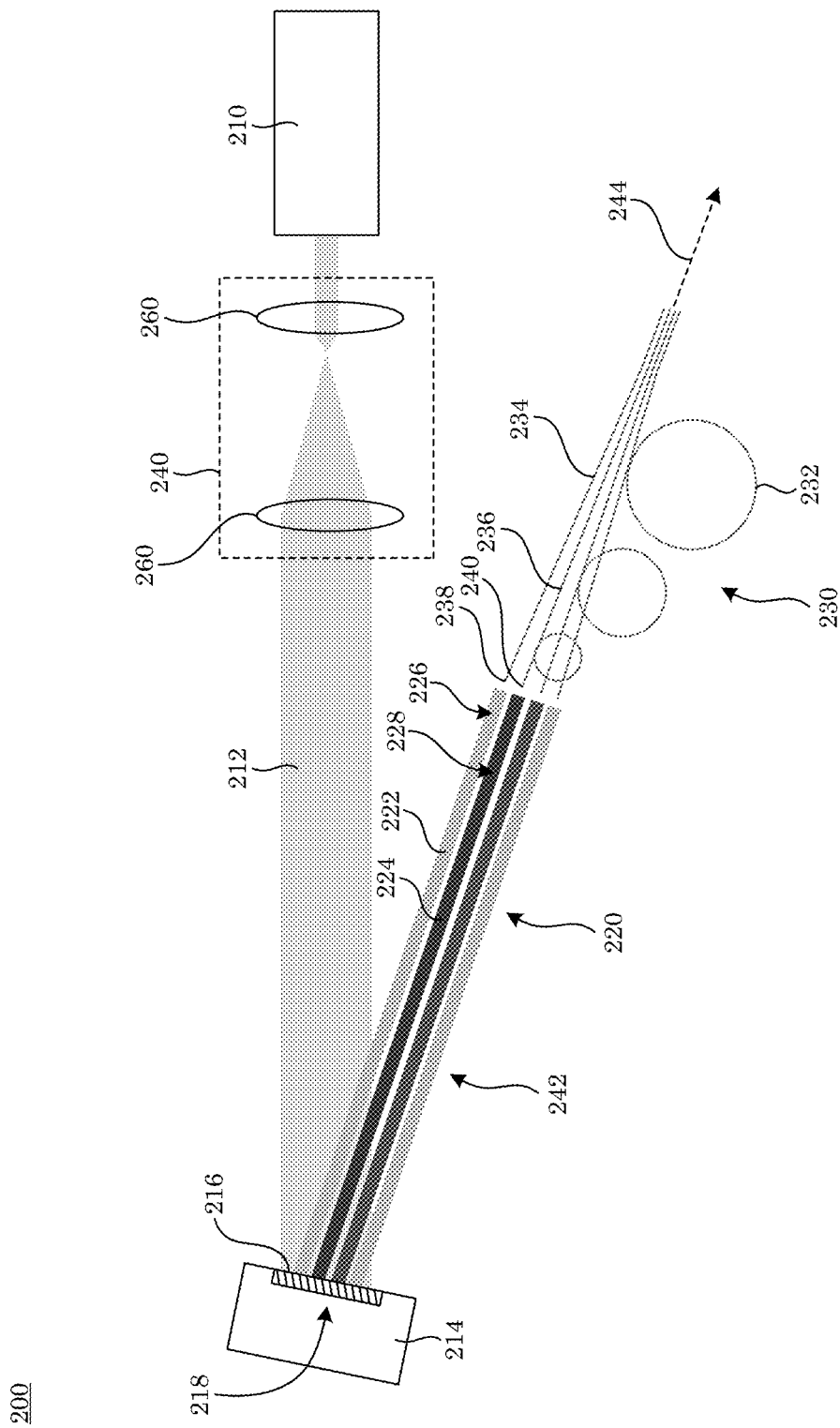
FIG. 2 shows an optical phantom.

With reference to FIG. 2, optical phantom 200 can include telescope 246 interposed between light source 210 and spatial light modulator 214, such that telescope 246 receives first light 212 from light source 210 and enlarges a cross-sectional area of first light 212 to cover a selected portion of mirrors 216. Telescope 246 can include optical elements such as lens 260 to enlarge, collimate, focus, or decrease a size of first light 212.

Figure 3:
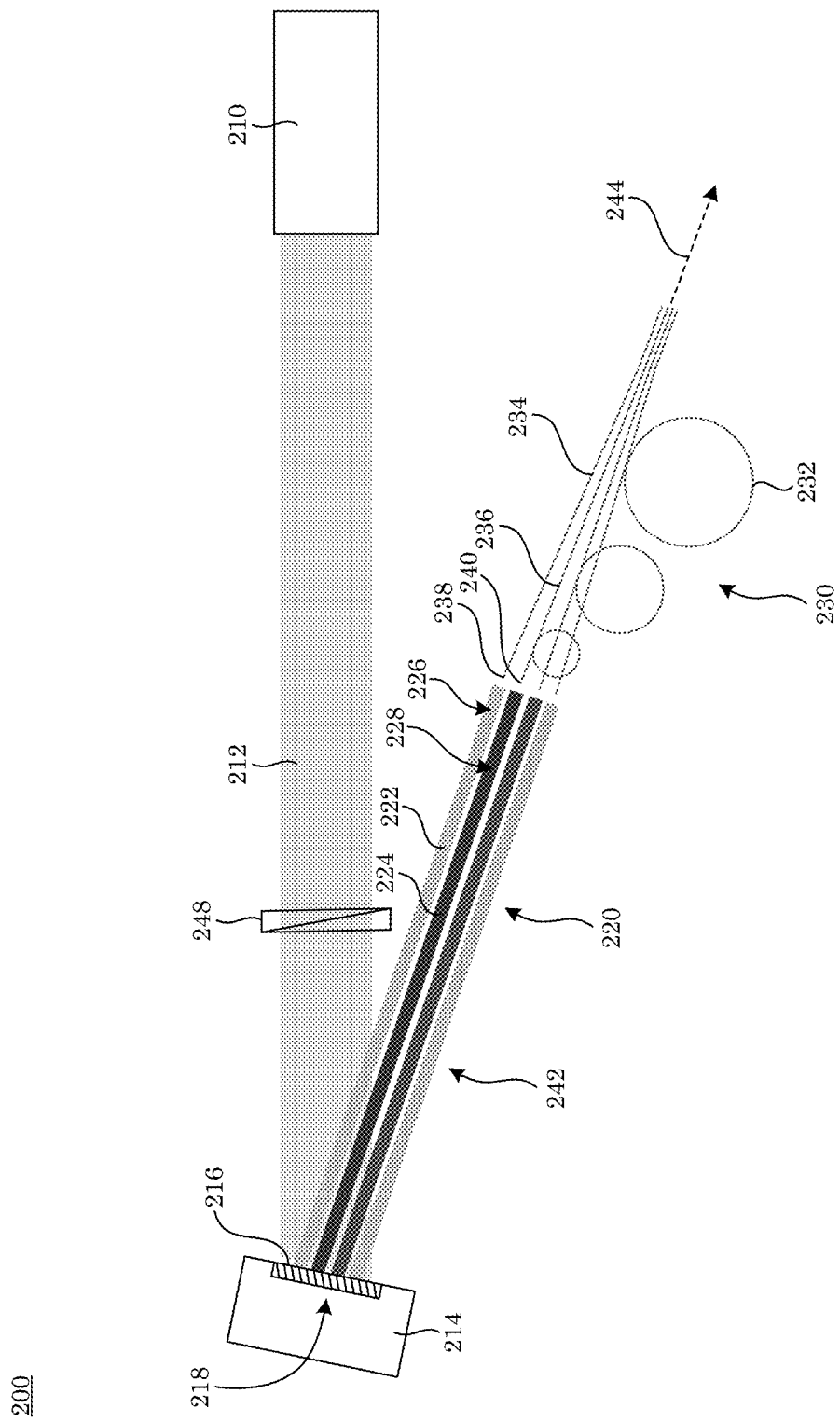
FIG. 3 shows an optical phantom.

With reference to FIG. 3, optical phantom 200 can include polarizer 248 interposed between light source 210 and spatial light modulator 214, such that polarizer 248 receives first light 212 from light source 210 and selectively polarizes first light 212 to be received by mirrors 216.

Figure 4:
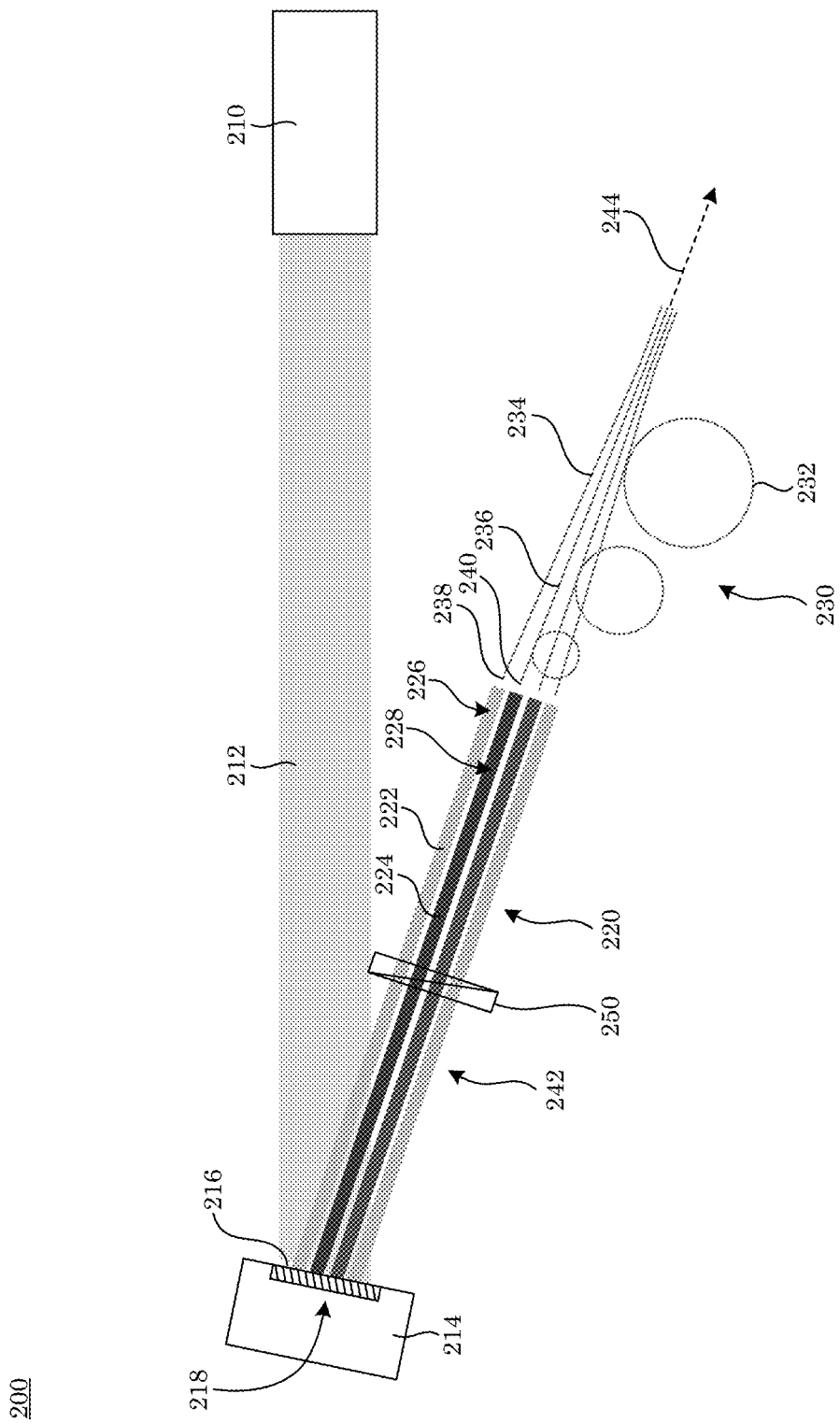
FIG. 4 shows an optical phantom.

With reference to FIG. 4, optical phantom 200 can include polarizer 250 interposed between spatial light modulator 214 and optical delay line 230, such that polarizer 250 receives filtered light 242 from spatial light modulator 214 and selectively polarizes filtered light 242 to be received by optical delay fibers 232 of optical delay line 230.

Figure 5:
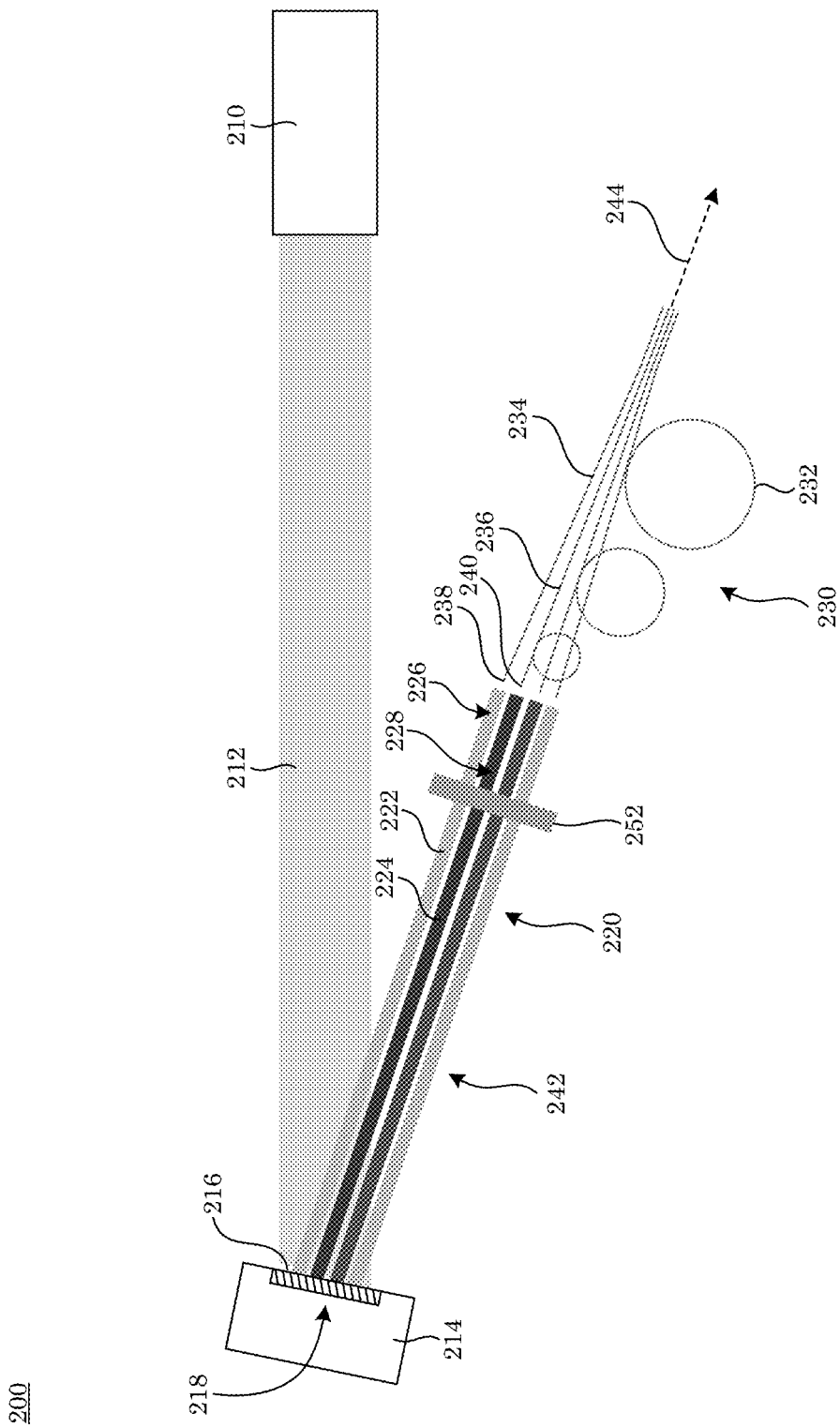
FIG. 5 shows an optical phantom.

With reference to FIG. 5, optical phantom 200 can include optical density filter 252 interposed between spatial light modulator 214 and optical delay line 230, such that optical density filter 252: receives filtered light 242 from spatial light modulator 214; increases a contrast between first photon flux 226 and second photon flux 228; and communicates first photon flux 226 and second photon flux 228 with increased contrast to optical delay line 230.

Figure 6:
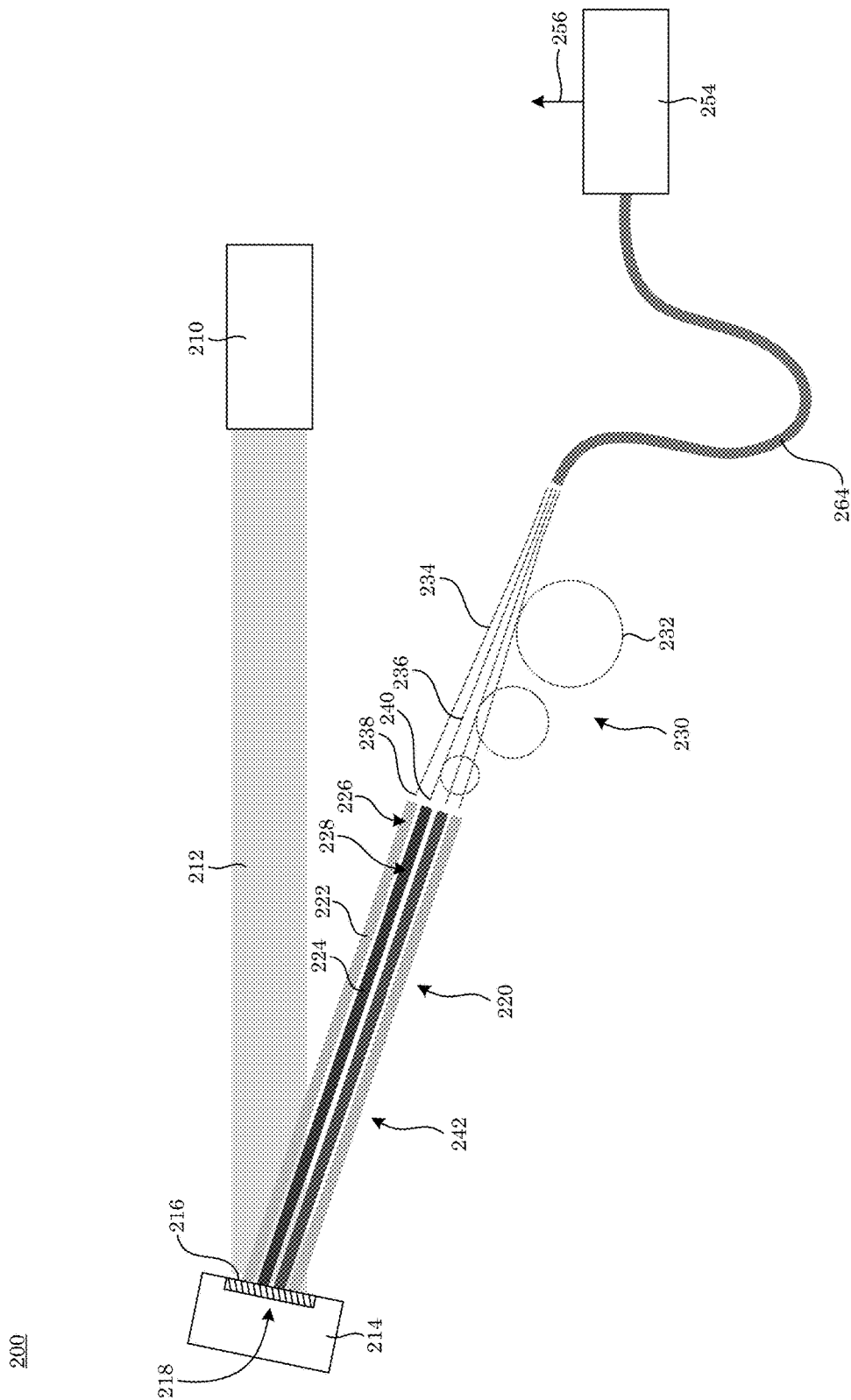
FIG. 6 shows an optical phantom.

With reference to FIG. 6, optical phantom 200 can include light detector 254 in optical communication with optical delay line 230 to receive phantom light 244 communicated from optical delay fibers 232 and to produce time-of-flight signal 256 from first photon flux 226 and second photon flux 228.

Figure 7:
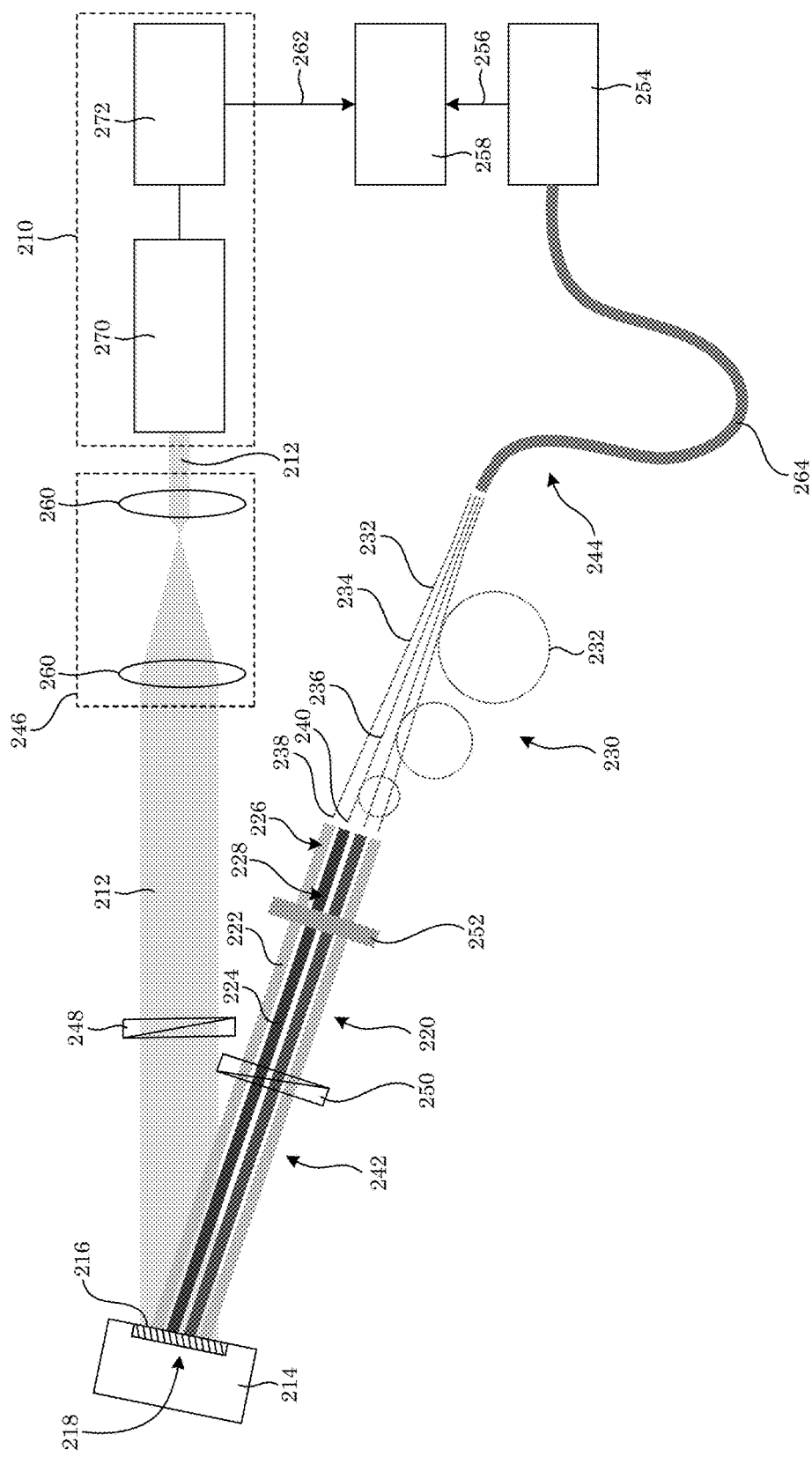
FIG. 7 shows an optical phantom.

With reference to FIG. 7, optical phantom 200 can include time correlator 258 in communication with light detector 254 and light source 210 and that: receives time-of-flight signal 256 from light detector 254; receives timing signal 262 from light source 212; and correlates first time-of-flight distribution 402a and second time-of-flight distribution 402b with timing signal 262 from light source 210. Individual light pulses of filtered light propagating through optical delay line 230 through optical delay fibers 232 (e.g., 24, 236, and the like) can be combined in a single optical fiber such as common optical fiber 264 interposed between optical delay line 230 and light detector 254 such that phantom light 244 is produced by combining individual time-of-flight distributions of filtered light delayed by optical fibers 232.

It is contemplated that light source 210 is in optical communication with spatial light modulator 214 and can include laser 270 that provides first light 212. Laser 270 can receive a control signal from laser driver 272 that also communicates timing signal 262 to time correlator 258. In this manner, a wavelength, repetition rate, pulse width, a duty cycle of laser 270 can be selected such that light source 210 produces a picosecond pulse of first light 212. Light detector 254 is selected to detector phantom light 244 and can be, e.g., a photomultiplier, photodiode, phosphor plate, microchannel plate, scintillator, or a combination thereof.

Figure 8:
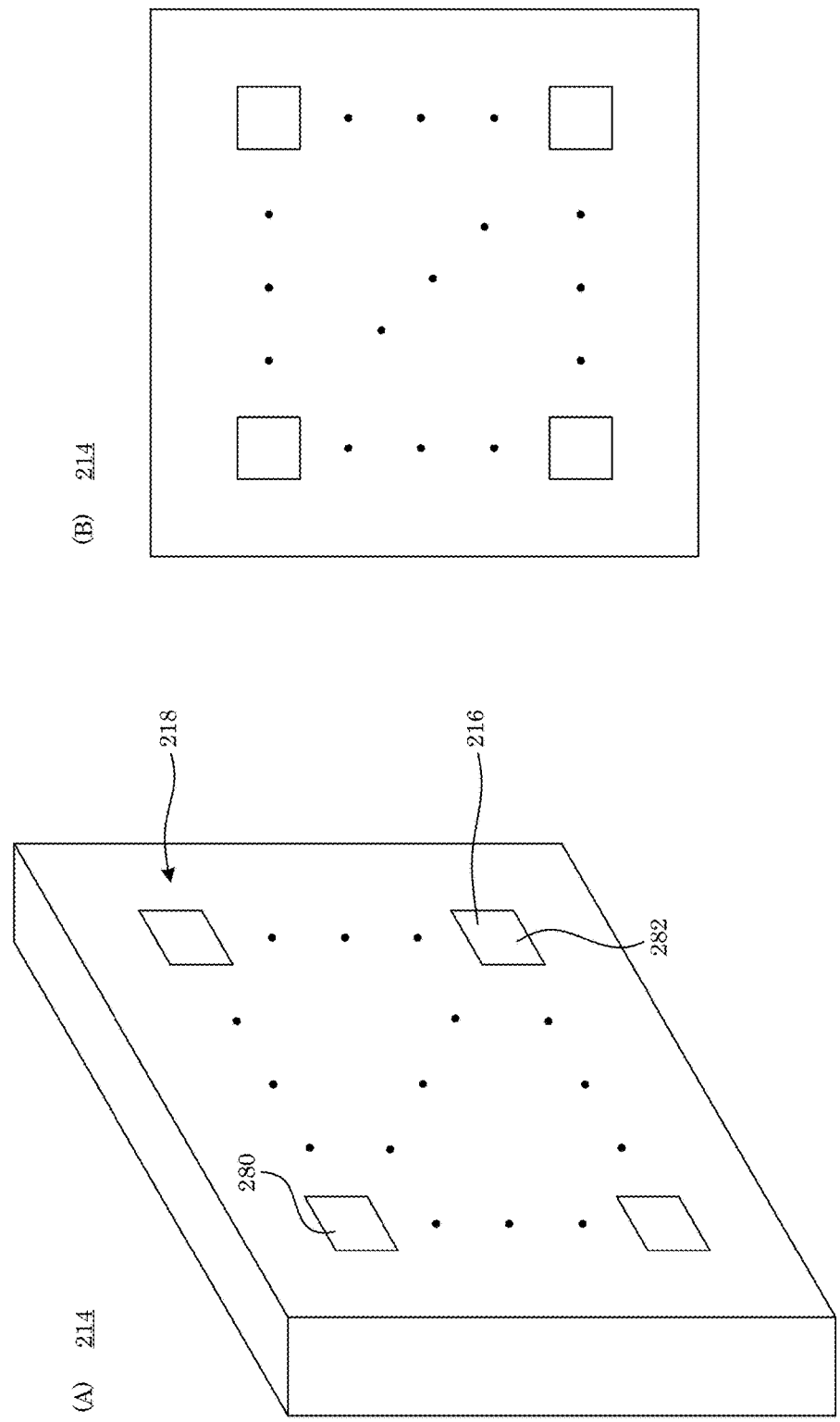
FIG. 8 shows a filter device that includes a spatial light modulator.

Spatial light modulator 214, with reference to FIG. 8, includes mirrors 216 arranged in array 218 such that mirrors 216 (e.g., first mirror 280, second mirror 282) are individually controllable to selectively reflect first light 212 as filtered light 242. Additionally, first mirror 280 can provide filtered light 242 along first light path 222 to first delay fiber 234 while second mirror 282 independently provides filtered light 242 along second light path 224 to second delay fiber 236. Accordingly, with reference to FIG. 9, light source 210 produces first light 212 having initial TOFD 400 as shown in panel A. Spatial light modulator 214 produces a plurality of light paths, wherein filtered light 242 propagating along individual light paths have a selected and independent intensity, and optical delay line 230 individually temporally delays filtered light 242 to produce individual TOFDs 402a, 402b, . . . , 402n (wherein n is an arbitrary integer, e.g., 2, 3, . . . , 1000) with selected intensities I1, I2, . . . , $I_n$) shown in panel B of FIG. 9 that are combined by common fiber 264 to produce phantom light 244 having time-resolved diffuse reflectance spectrum 404 shown in panel C of FIG. 9.

A process for making optical phantom 200 can include providing laser 270; connecting laser driver 272 to be in optical communication with laser 270; disposing telescope 246 in optical communication with light source 210 to receive first light 212 from laser 270; disposing polarizer 248 in optical communication with light source 210 to receive first light 212 from laser 270; disposing spatial light modulator 214 in optical communication with light source 210 to receive first light 212 from laser 270; disposing polarizer 250 in optical communication with spatial light modulator 214 to receive filtered light 242 from spatial light modulator 214; disposing optical density filter 252 in optical communication with spatial light modulator 214 to receive filtered light 242 from spatial light modulator 214; disposing optical delay line 230 in optical communication with spatial light modulator 214 to receive filtered light 242 from spatial light modulator 214 and to produce phantom light 244; disposing common fiber 264 in optical communication with optical delay line 230 to produce phantom light 244; disposing light detector 254 in optical communication with optical delay line 230 to receive phantom light 244; disposing time correlator 258 in communication with laser driver 272 and light detector 254 to receive time-of-flight signal 256 from light detector 254 and to receive timing signal 262 from laser driver 272.

According to an embodiment, a process for producing time-resolved diffuse reflectance spectrum 404 with optical phantom 200 includes: producing first light 212; subjecting first light 212 to spatial filtering or to intensity to produce filtered light 242; subjecting filtered light 242 to temporal delay with optical delay line 230 to produce phantom light 244 including the time-resolved diffuse reflectance spectrum 404.

In an embodiment, a process for testing measuring device 26 (e.g., an oximeter) includes: producing phantom light 244 including time-resolved diffuse reflectance spectrum 404; comparing phantom light 244 to tissue photon time-of-flight distribution 22 from measuring device 26; and determining whether measuring device 26 is operating at an acceptable performance level based on the comparison between tissue photon time-of-flight distribution 22 and time-resolved diffuse reflectance spectrum 404.

Figure 10:
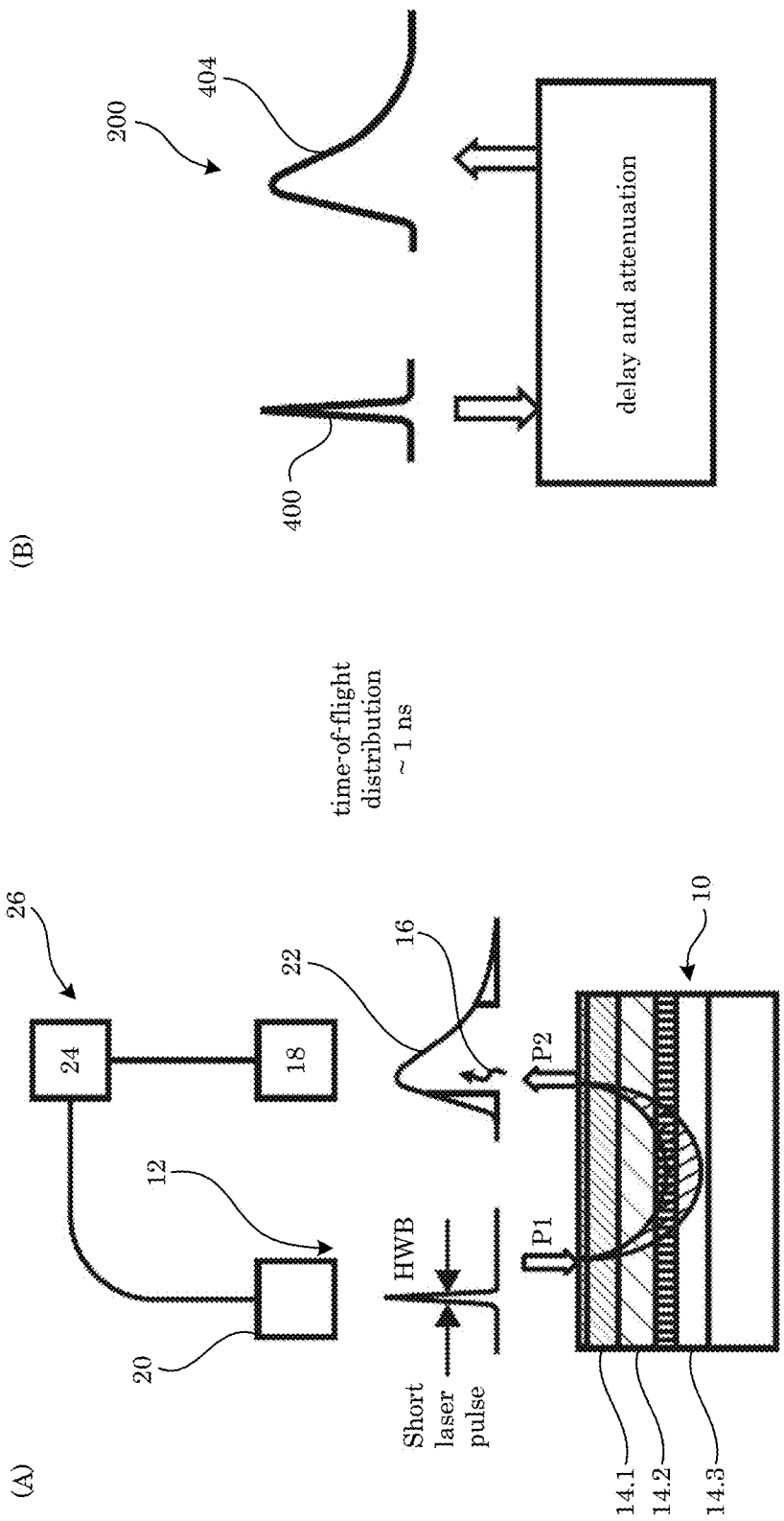
FIG. 10 shows an input light pulse propagating through biological tissue and output photons exiting the biological tissue in panel A, and panel B shows an optical phantom that produces first light and phantom light.

Advantageously, with reference to panel A of FIG. 10, optical phantom 200 tests measuring device 26 that performs time-resolved diffuse optical spectroscopy on biological tissue 10. Measuring devices 26 are used in medical diagnostics. For taking a measurement value, measuring device 26 emits light pulses 12 into biological tissue 10. Light pulse 12 propagate in biological tissue 10 and exit biological tissue 10. During propagation in biological tissue 10, photons in light pulse 12 are scattered and, upon exiting biological tissue 10, an amount of light detected by detector 18 of measuring device 26 can be very small. Depending on how many scattering events subjected to light pulse 12 from measuring device 26 in biological tissue 10 and a length of a path of propagation of light pulse 12 in biological tissue 10, different delay times occur between input light pulse 12 from measuring device 26 and a time at which photons exit biological tissue 12 and are detected. To obtain a measurement value by measurement device 26, a time resolution of the time-of-arrival of photons at detector 18 is in the picosecond range.

Measurement device 26 is validated to determine whether the measurement value obtained from measurement device 26 has desired accuracy. Validation can be done by comparison with a reference value. For measuring device 26, such as a cerebral oximeter, the measurement value can be oxygen saturation in the brain. For conventional in vivo validation, an amount of oxygen in the respiratory air is reduced and then provided to subjects, and the altered cerebral oxygen saturation is measured. Conventionally, the reference value for oxygen saturation to be measured in the brain is formed from the oxygen saturation of blood in a jugular vein, which involves drawing venous blood from the brain. Blood samples from the jugular vein near a base of a skull or an artery on an arm are drawn and analyzed by blood gas analysis. The conventional reference value is created, such as 0.75 times jugular venous oxygen saturation plus 0.25 times arterial oxygen saturation value. The oxygen supply is changed for a subject to record measurements over a range of oxygen saturation.

Instead of using a jugular catheter, a physical phantom can be used, wherein the physical phantom can include erythrocytes in a scattering fluid in which oxygen saturation of hemoglobin can be changed by gas exchange or yeast. Physical phantoms can be complex and produce results that are difficult to reproduce. In addition, modelling results from physical phantoms can be arduous, and results for multiple biological tissue layers sample or more complex biological tissue structures can be untenable to obtain or reproduce.

Advantageously, optical phantom 200 herein tests performance of measuring device 26 used for time-resolved diffuse optical spectrometry. Optical phantom 200 can include input optic 30 in optical communication with light supply lines 32; filter device 34 in optical communication with light supply lines 32 and disposed in a direction of propagation of light from light supply lines 32; and optical delay line 230 in optical communication with filter device 34 and including a plurality of optical delay fibers 232. Optical delay fibers 232 are arranged relative to filter device 34 such that light received by each optical delay fiber 232 is individually filtered by filter device 34, and optical delay fibers 232 are joined to receive light leaving filter device 34 such that optical delay line 230 produces phantom light 244 with time-resolved diffuse reflectance spectrum 404 in response to receiving first light 212 with initial time-of-flight distribution 400 at input optic 30. Optical delay fibers 232 have different optical path lengths $w_i$ for light such that output pulse lengths of photon intermediate time-of-flight distributions 402 (e.g., first time-of-flight distribution 402a, second time-of-flight distribution 402b, and the like) from optical delay fibers 232 are greater than an input pulse length of first light 212. A combination of optical delay line 230 and filter device 34 provides time-resolved diffuse reflectance spectrum 404 that mimics a photon time-of-flight distribution produced by biological tissue 10 upon subjecting biological tissue 10 to a pulse of light, e.g., probe light 12, from measuring device 26.

According to an embodiment, a method for producing phantom light 244 having time-resolved diffuse reflectance spectrum 404 for testing measuring device 26 for time-resolved diffuse optical spectroscopy of biological tissue 10, includes: illuminating filter device 34 with input light pulse 400 from light source 220 communicated through input optic 30, wherein each filter element 36 of filter device 34 receives photons as a partial light pulse from input light pulse 400 incident on filter device 34; filtering the partial light pulses by filter device 34, wherein a filter transmission F varies for at least one of the partial light pulses; guiding the partial light pulses along optical paths $w_i$ of optical delay lines 232 having different lengths in optical delay line 230; and merging the partial light pulses by light collector 38 that is in optical communication with filter device 34 and arranged in a direction of light propagation, such that phantom light 244 exit an output surface of optical delay line 230, wherein the optical paths $w_i$ are selected and filtering is conducted such that a time-resolved diffuse reflectance spectrum 404 of phantom light 244 mimics tissue photon time-of-flight distribution 22 produced from subjecting a biological tissue 10 to probe light 12 (see panel A of FIG. 10).

Advantageously, input light pulse 400 of first light 212 is changed by propagating through different length optical paths provided by optical delay line 230 and selective filtering by filter device 34 that mimics light propagation in biological tissue 10, e.g., human biological tissue. Optical phantom 200 tests measuring device 26 without in vivo measurements on a subject. Calculating scattering and absorption effects on photon time-of-flight distribution in biological tissue 10 can be based on a mathematical model and that can be compared to results from optical phantom 200. Moreover, results with phantom light 244 from optical phantom 200 can be mathematically convolved to predict scattering and absorption by biological tissue 10 so that performance of measuring device 26 such as an oximeter can be assessed. Advantageously, through such calculation, measurement values can be calculated for a subject for a property such as low oxygen in the brain. Beneficially, for in vivo data for validation, repeated measurements are superfluous, wherein measurement values for response of biological tissue 10 to input light pulse 12 can be temporally or spatially reproduced as desired.

Measuring device 26 for time-resolved diffuse optical spectroscopy emits input light pulses 12 from source optode 20 to biological tissue 10, and measuring device 26 can include detector 18 for detecting output photons 16 in tissue photon time-of-flight distribution 22 and a position of photons 16 exiting biological tissue 10 at several wavelengths from which can be calculated a concentration of a chromophore, e.g., hemoglobin, deoxyhemoglobin, and the like. Exemplary calculations include hemoglobin oxygen saturation in biological tissue 10 or deoxyhemoglobin concentration, which can be calculated as a function of wavelength.

In a time-resolved diffuse optical measuring device 26 such as a cerebral oximeter, cerebral oximeter 26 measures oxygen saturation of blood in the brain non-invasively through the skull. Alternatively, measuring device 26 can also measure oxygen saturation of blood in a muscle or organ, hemoglobin concentration, concentration of another chromophore such as cytochrome-c oxidase, and the like. The chromophore can be a marker that is absorbed by tumor cells. Measuring device 26 can have a picosecond time resolution. A pulse response function of measuring device 26 (without pulse broadening in the test object) can be due to a laser 20 pulse width and time resolution of detector 18 and detection electronics with a full-width at half maximum (FWHM), i.e., a half-width, in a picosecond range for detection of a time-of-flight distribution with a temporal increment of a few picoseconds, e.g., from 1 ps to 25 ps.

Filtering (i.e., optical or light filtering) can include reducing an intensity of light and can be similar to absorbing a portion of incident photons. Input optics 30 can include a lens, polarization optic, or a combination thereof. The polarization optic can impart polarization to incident light. Filter device 34 can have a line-shaped or matrix-shaped filter element 36 and plurality of filter elements (e.g., 36a, . . . , 36n, wherein n can correspond to an arbitrary integer so that there can be an arbitrary number of filter elements).

It is contemplated that optical delay line 230 and filter device 34 provide an output pulse length of time-resolved diffuse reflectance spectrum 404 of phantom light 244 that is, e.g., four times greater than an pulse length of first light 212 with initial time-of-flight distribution 400, e.g., 250 picoseconds. In an embodiment, an output pulse length of time-resolved diffuse reflectance spectrum 404 is a nanosecond when a delta function input light pulse of first light 212 is communicated to input optic 30.

According to an embodiment, optical fibers 232 and filter device 34 provide a photon TOFD that corresponds to a delta-function shaped input light pulse and that mimics a time-resolved in vivo measurement of human biological tissue 10 for a physiological property such as, e.g., an oxygen saturation. In this way, optical phantom 200 mimics a measurement of photon time-of-flight distributions through human biological tissue as tissue photon time-of-flight distribution 22.

In an embodiment, filter device 32 is controlled to selectively provide filtered light 242 to optical fibers 232 of optical delay line 230. Here, filter device 34 can include a liquid crystal array in which individual filter elements 36 (e.g., pixels) of the liquid crystal array are controlled. By varying an interaction of pixels 36 with first light 212 from input optic 30, optical phantom 200 can mimic characteristics of photon propagation through biological tissue 10 or a photophysical property of biological tissue 10. In this manner, changing oxygen saturation can be simulated. Filter device 34 can be controlled by electrical signals in which a voltage change provided to pixel 36 changes an amount of filtered light 242 provided to optical fibers 232 from pixel 36.

In an embodiment, filter device 36 is controlled so that filter transmission F is adjustable for a majority of first light 212 to change a shape (e.g., width a temporal amplitude profile) of time-resolved diffuse reflectance spectrum 404 of phantom light 244. Filter transmission F can be automatically generated for filtered light 242, e.g., by an electrical signal provided to filter device 34.

In an embodiment, filter device 34 is a spatial light modulator 214 such as a liquid crystal light modulator. Filter device 34 can include a beam splitter or polarizer so that first light 212 incident on input optic 30 is polarized and positioned below a liquid crystal matrix of spatial light modulator 214. Pixels 36 can rotate polarization. Depending on the polarization rotation of each pixel 36, an intensity of light transmitted by a second polarizer can be varied. In this way, along with a step-wise delay in light delivery, a selected time-resolved diffuse reflectance spectrum 404 can be made via production of intermediate time-of-flight distributions 402.

Light lines (e.g., light supply line 32, optical fibers 232) can have a gradient in an index of optical refraction and can be optical fibers that temporally spread filtered light 242 through particular delay fiber through which filtered light 242 propagates. A variation of optical path length (wi) in the delay fibers 232 is achieved by gradient index optical fibers that physically have different lengths. An increment of a length difference among delay fibers 232 of the optical delay line 230 can be selected to correspond to a temporal width of a time channel used for detecting TOFDs (e.g., intermediate time-of-flight distributions 402 or time-resolved diffuse reflectance spectrum 404) of phantom light 244 detected by light detector 254. An increment of time delay of 20 ps can be provided by an increment of length of delay fiber 232 of 4 mm for a refractive index of the optical fiber of delay fiber of 1. A time range for a time-of-flight distribution of photons through optical delay line 230 can be provided by optical delay line 230 having, e.g., 100 optical fibers arranged as delay fibers (e.g., 234, 236) of such step-wise different lengths.

A dynamic range of filter transmission F of filter device 34, e.g., spatial light modulator 214, can be from 1:100 to 1:1000 and can mimic an intensity for tissue photon time-of-flight distribution 22. A transmittance of optical phantom 200 can correspond to an amount of diffuse reflection or transmission of biological tissue 10. For a distance from light source 20 to detector 18 that is 3 cm, e.g., for measurements on a subject's head, a total diffuse reflectance is $5 \times 10^3$ mm$^{-2}$, as summed over tissue photon time-of-flight distribution 22, for a photon flux of 0.005 photons per mm$^2$ exiting from biological tissue 10. To mimic this value and provide a reference value, optical phantom 200 can include a filter interposed between light source 210 and light detector 254 to attenuate light for optical delay line 230, e.g., equal attenuation for light entering each optical fiber 232 (e.g., delay fibers 234, 236).

In an embodiment, optical phantom 200 includes an electrical controller that controls spatial modulator 214. The electrical controller can have a digital memory in which control data are stored and which automatically control operation of spatial light modulator 214. In this manner, spatial light modulator 214 can automatically and selectively communicate filtered light 242 to optical delay line 230 so that a selected time-resolved diffuse reflectance spectrum 404 produced by optical phantom 200 mimics tissue photon time-of-flight distribution 22 through biological tissue 10. Reference values can be determined experimentally or calculated using a model.

In an embodiment, optical phantom 200 includes optical delay fibers (e.g., 234, 236) arranged relative to spatial light modulator 214, wherein delay fibers 232 are disposed in optical delay line 230 for each element of spatial light modulator 214 such that each delay fiber 232 is positioned to receive filtered light 242 communicated from spatial light modulator 214. In this way, first light 212 has an intensity that can be attenuated by a selected, adjustable amount by spatial light modulator 214 such that time-resolved diffuse reflectance spectrum 404 can be obtained by combination of spatial light modulator 214 and optical delay line 230.

A process for testing measuring device 26 for time resolved diffuse optical spectroscopy of tissue 10 includes: producing first light 212 on input optic 30 of optical phantom 200; collecting phantom light 244 that exit optical phantom 200; determining a measurement value, e.g., a measured oxygen saturation of hemoglobin in tissue 10, from tissue photon time-of-flight distribution 22 measured for at least two wavelengths by measuring device 26; and comparing the measurement value with a reference value for hemoglobin oxygen saturation of blood in biological tissue 10, wherein the reference value was determined together with time-resolved diffuse reflectance spectrum 404 in an experimental set-up, and wherein time-resolved diffuse reflectance spectrum 404 mimics tissue photon time-of-flight distribution 22. In this way, measuring device 26 is subjected to testing by optical phantom 200 without performing in vivo measurements on subjects.

According to an embodiment, optical phantom 200 includes input optic 30 having light supply lines 32, filter device 34 in optical communication with light supply lines 32 to receive light from light supply lines 32 such that light from each light supply line 32 is filtered individually by filter device 34, and optical delay line 230 in optical communication with filter device 34 and that receives filtered light 242 from filter device 34, wherein optical delay fibers 232 of optical delay line 230 are a different length such that optical delay fibers 232 provide different intermediate time-of-flight distributions 402 from filtered light 242 propagating through different optical delay fibers 232. In this manner, pulse length of time-resolved diffuse reflectance spectrum 404 is greater than a pulse length of initial time-of-flight distribution 400 to test operation of measuring device 26, e.g., a time-resolved diffuse optical spectrometer such as a biological tissue oximeter.

Panel A of FIG. 10 shows behavior of biological tissue 10 when input pulse of probe light 12 is delivered to biological tissue 10. Biological tissue 10 can be a plurality of cells such as animal cells, including human cells. Biological tissue 10 can include a plurality of stacked biological tissue layers 14 such as that found in a head. Exemplary biological tissue layers 14 can include first biological tissue layer 14a such as a scalp, second biological tissue layer 14b such as a skull, third biological tissue layer 14c such as a cortex of a human or animal biological tissue 14.

Probe light 12 is received by biological tissue 10, and probe light 10 interacts with biological tissue 10. Probe light 12 enters at first location P1 of biological tissue 10 and exits biological tissue 10 at second location P2. A pulse shape of probe light 12 or first light 12 can be a delta-function that has a FWHM, e.g., of 250 picoseconds. A wavelength of first light 212 or probe light 12 can be monochromatic or polychromatic.

At second location P2 output photons 16 exit biological tissue 10 and can be detected by detector 18. Second location P2 is at distance r from first location P1.

The time-of-flight varies depending on how many scattering events have occurred for probe light 12 propagating in biological tissue 10. A time-of-flight between emission of probe light 12 by source 20 at time T0 and arrival of output photons 16 from biological tissue 10 at detector 18 at arrival time TA is Δt=TA−T0.

Figure 11:
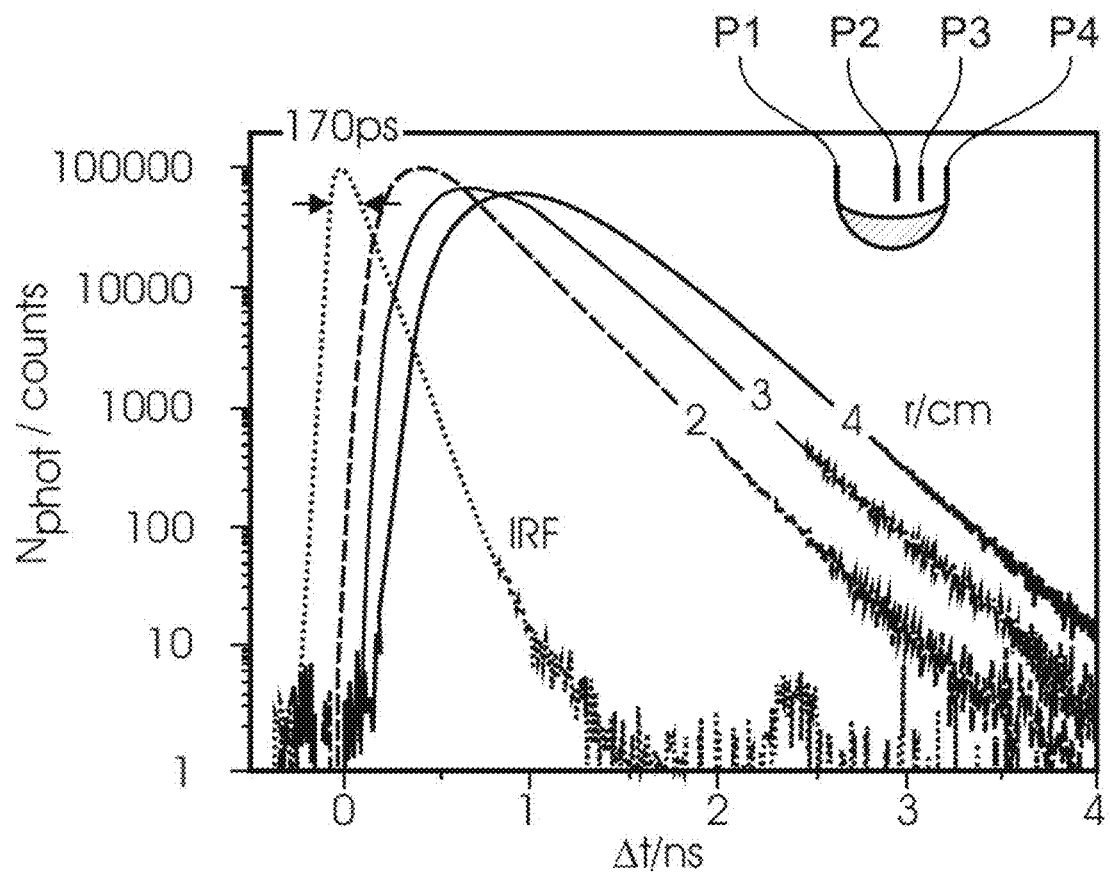
FIG. 11 shows a plurality of photon TOFDs as a function of distance r between initial location P1 at which tissue is subjected to an input light pulse of input photons and a location (P2, P3, P4) from which output photons exit the biological tissue and are detected.

Probe light 12 can be subjected to scattering and absorption in biological tissue 10 that leads to output photons 16 exiting biological tissue 10 out of an area on a surface of biological tissue 10 instead of a single point location. Accordingly, as shown in FIG. 11, output photons 16 can exit biological tissue in the area on the surface and can be detected over all of the area or a portion of the area. TOFDs of output photons 16 from different locations, e.g., second location P2, third location P3, fourth location P4, and the like, can be acquired by detector 18 and are shown in FIG. 11. Due to longer optical path lengths or photophysical processes TOFDs and peak arrival times for P2, P3, and P4 differ and have increasing delay times, i.e., longer flight times that cause larger time-of-flight Δt.

With larger time-of-flight Δt, more scattering or absorption may have occurred to probe light 12 in biological tissue 10. As a result, tissue photon time-of-flight distribution 22 is an asymmetric time distribution about its maximum value. Photon TOFD can be used to determine a property of biological tissue 10 such as oxygen saturation of biological tissue 10.

FIG. 11 shows a graph of a logarithm of a number of output photons 16 versus time-of-flight Δt, wherein TOFDs are shown for different distances r between source optode 20 at the first location P1 and detector optode 18 at location P2, P3 or P4. TOFD for probe light 12 is shown as a dashed curve, and zero time-of-flight Δt=0 FIG. 11 occurs at a maximum value for the TOFD of probe light 12.

Panel A of FIG. 10 shows measuring device 26 that includes detector optode 18 and source optode 20 in communication with measurement and evaluation unit 24 for time-resolved diffuse optical spectroscopy of biological tissue 10. It is contemplated that measuring device 26 determines a concentration of a chromophore, e.g., hemoglobin, oxyhemoglobin, deoxyhemoglobin, and the like, from tissue photon time-of-flight distribution 22. A repetition frequency of probe light 12 or first light 212 can be, e.g., 10 MHz, 40 MHz, and the like.

Per pulse of probe light 12, a single output photons 16 can be detected from which tissue photon time-of-flight distribution 22 can be determined over a number of pulses of probe light 12. Tissue photon time-of-flight distribution 22 can be determined from time-correlated single photon counting that provides a histogram of the time-of-flight times that for a plurality of output photons 16 provide tissue photon time-of-flight distribution 22. A measurement time can be, e.g., 300 milliseconds (ms), 1 second (s), and the like.

Figure 13:
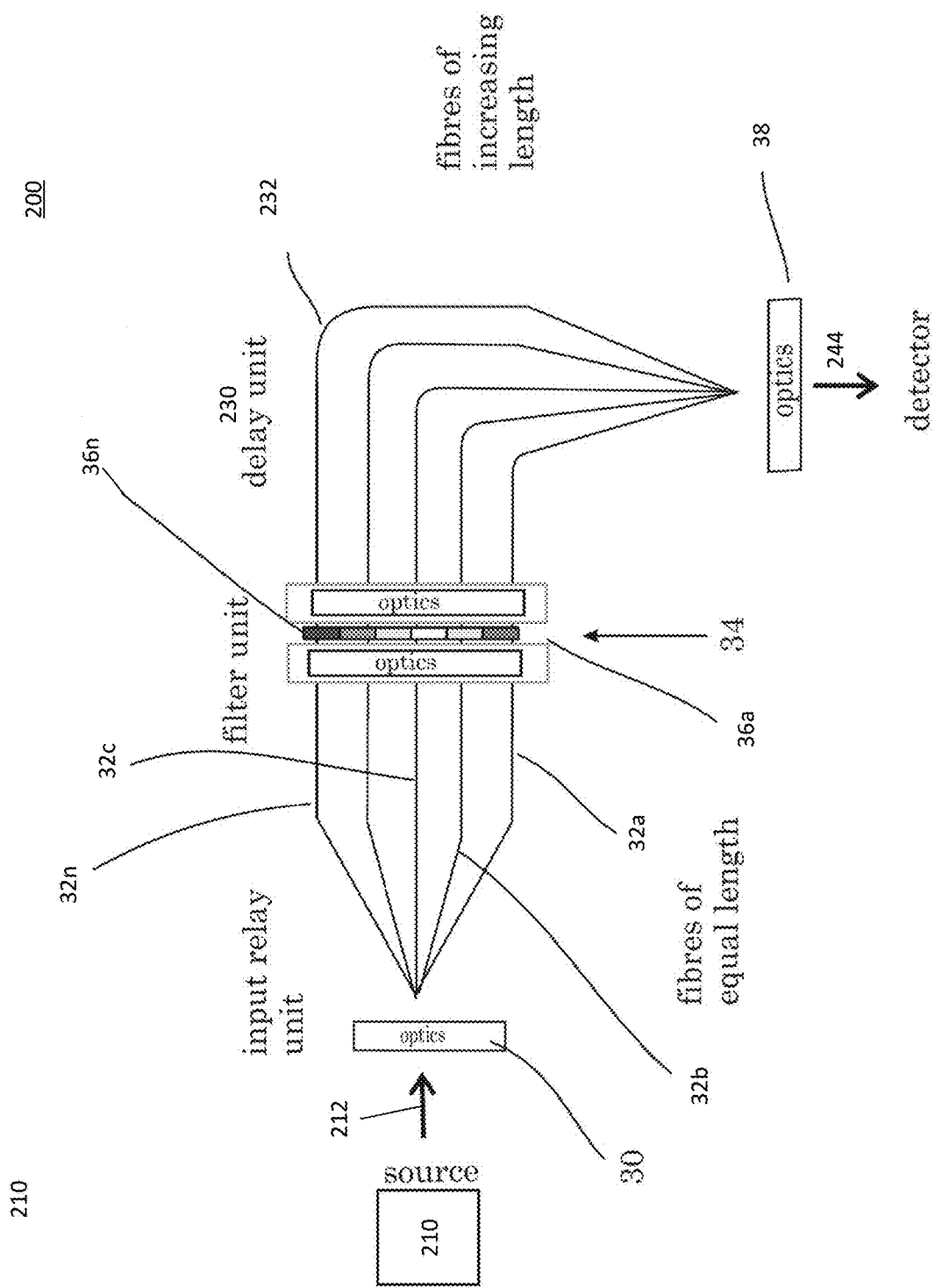
FIG. 13 shows an optical phantom.

FIG. 13 shows an embodiment of optical phantom 200 for testing measuring device 26. Optical phantom 200 has input optic 30, a plurality of light supply lines 32 (e.g., 32a, . . . , 32n, an arbitrary number of light supply lines. Input optic 30 is irradiated with first light 212, in which light flux of first light 12 is split among light supply lines 32 and communicated to filter device 34. Filter device 34 has a plurality of pixels 36 (e.g., 36a, . . . , 36n, an arbitrary number of pixels or filter elements) in which first pixel 36a corresponds to light supply line 32, . . . , n-th pixel 36n corresponds to n-th light supply line 32n so that light from a particular pixel 36i receives first light 212 from particular light supply line 32i. Optical delay line 230 is in optical communication with filter device 34 and includes a plurality of optical fibers 232 as delay fibers, e.g., first delay fiber 234, second delay fiber 236, and the like. Filtered light 242 emerging from a particular pixel 36i enters a particular optical delay fiber 232. Light from optical fibers 232 of optical delay line 230 is combined to produce phantom light 244 and emerge from and can be communicated to light detector 254, e.g., via optic 38.

Optical paths $w_i$ through which light propagates through optical fibers 232 of optical delay line 230 differ in length so that a plurality of intermediate time-of-flight distributions 402 are produced, wherein individual intermediate time-of-flight distributions 402 have a selected intensity due to selected filter transmission $F_i$ of individual pixels 36 of filter device 34.

Figure 12:
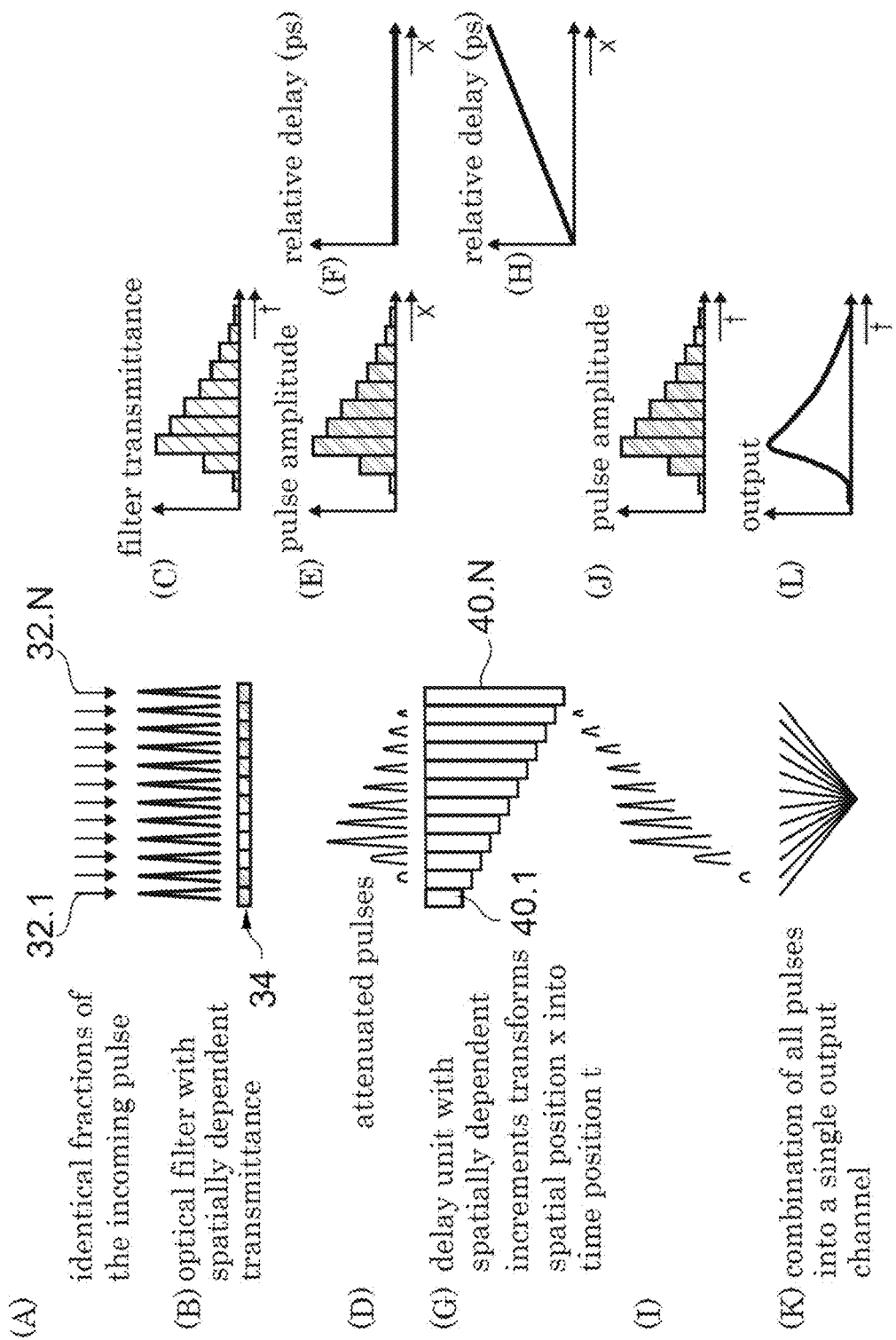
FIG. 12 shows changes in TOFDs and intensity of light in an optical phantom.

FIG. 12 shows operation of optical phantom 200. Panel A shows first light 12 propagating through light supply line 32. Panel B shows identical pulses of first light 12 incident at filter device 34 with similar arrival times, wherein filter device 34 has selected filter transmission F profile shown in panel C. Panel D shows filtered light 242 having different intensity but similar arrival times at optical delay line 230. Panel E shows a histogram of pulse amplitudes for filtered light 242 after filter device 34, and panel F shows that different components of filtered light 242 shown in panel D have not relative delay among them. Panel G shows different lengths of optical delay fibers 232 of optical delay line 230, and panel H shows a relative delay profile of optical delay fibers 232. Panel I shows a plurality of intermediate time-of-flight distributions 402 for light exiting optical delay line 230 shown in panel G in which early arrival times are at a bottom of panel I, and later arrival times are at a top of panel I with respect to time-of-arrival at optic 38. Panel J shows pulse amplitudes for a time-of-arrival histogram of intermediate time-of-flight distributions 402 shown in panel I. Panel K shows optical fibers that combine light from optical delay line 230 of panel G to produce phantom light 244 having time-resolved diffuse reflectance spectrum 404 shown in panel L. time-resolved diffuse reflectance spectrum 404 mimics tissue photon time-of-flight distribution 22 produced by probe light 12 passing through biological tissue 10.

It is contemplated that optical phantom 200 provides near-infrared (NIR) diffuse optical imaging or spectroscopy or tests measuring device 26 that performs near-infrared diffuse optical imaging or spectroscopy. NIR probe light 12 can penetrate into biological tissue 10 for several centimeters deep. Probe light 12 propagating in biological tissue 10 at a point on a surface of biological tissue 10 is distributed within biological tissue 10 due to scattering, and fractions of probe light 12 exiting as output photons 16 can be detected several centimeters apart. An amount of light arriving at detector 18 depends on absorption and scattering properties at a particular wavelength of probe light 12 in biological tissue 10.

When probe light 12 is continuous wave (CW) light, the measurement of output photons 16 determines attenuation of intensity of probe light 12 from source to detector subject to interaction with biological tissue 10. Time-domain methods having a time resolution for acquisition of output photons 16 in a picosecond (ps) time resolution range include short laser pulses of probe light 12 communicated to biological tissue 10. During light propagation in biological tissue 10, probe light 12 is attenuated and its TOFD is temporally broadened. A detection system for detecting output photons 16 or phantom light 244 can include time-correlated single photon counting, record time-resolved diffuse reflectance for a TOFD of output photons 16 exiting biological tissue 10. A time-of-flight of a photon through a turbid medium is correlated with penetration depth of the photon in the turbid medium, wherein a photon with a short total travel time propagates through a shallow region (less deep) in biological tissue 10 as compared to a photon that has a longer time-of-flight that propagates deeper in biological tissue 10. Accordingly, time-domain methods achieve depth resolution and distinguish between processes in the brain and in superficial tissue layers.

With regard to a cerebral tissue oximeter that is based on NIR spectroscopy (NIRS) and on measurements of diffuse reflectance at several wavelengths, a concentration of oxyhemoglobin or deoxyhemoglobin or oxygen saturation of blood in tissue can be determined. By performing measurements simultaneously but at different source-detection site separations, e.g., detecting output photons 16 at P2, P3, P4, and the like, depth selectivity is achieved. Validation of cerebral tissue oximeters is a timely issue with unmet challenges.

Time-domain measurements with optical phantom 200 overcomes challenges with validation of oximeters and mimics TOFDs such as those displayed FIG. 11. Light source 210 of optical phantom 200 provides a short (ps) light pulse of first light 212 with an intensity (e.g., photon count) as a function of time on a time scale in a picosecond to nanosecond range and a resolution of a few ps. While a conventional laser may emit a short pulse in a ps to ns range, such conventional lasers do not freely vary a temporal profile of output pulses, e.g. by electronic control, such as a semiconductor laser driven by ultrashort electrical pulses. Electrical pulses can be arbitrarily shaped by waveform generators, e.g., a pattern generator in a time range greater than 1 ns, corresponding to a maximum of 1 Gsps (gigasample per second).

It is contemplated that optical phantom 200 provides first light 212, filtered light 242, or phantom light 244 with time resolution (steps) of several ps; a time range of a few ns; and a dynamic range of at least 1000.

With reference to FIG. 12, first light 212 having a short pulse is homogeneously distributed across an filter device 34 that includes of array 218 of variable filter element 36, preferentially a liquid crystal spatial light modulator. A fraction of the first light 212 that is transmitted through individual filter element 36 is subjected to an individual filter transmittance. Filtered light 242 from filter device 34 includes a plurality of attenuated pulses of spatially varying amplitude. Optical delay line 230 includes spatially dependent delay fibers, wherein optical delay fibers 232 are arranged to spatially correspond to filter elements 36. Attenuated pulses of filtered light 242 experience an incremental delay in optical delay line 230 corresponding to their spatial position. In this way, the spatial position is transformed into a temporal position.

Components of phantom light 244 that have intermediate time-of-flight distributions 402 propagating from optical delay line 230 are combined into phantom light 244. The individual pulses of intermediate time-of-flight distributions 402 have different amplitudes and delays and are summed up to obtain a time-of-flight distribution as time-resolved diffuse reflectance spectrum 404, an optical waveform having a temporal profile (shape) determined by a selectable transmittance of filter elements of filter device 34.

Figure 14:
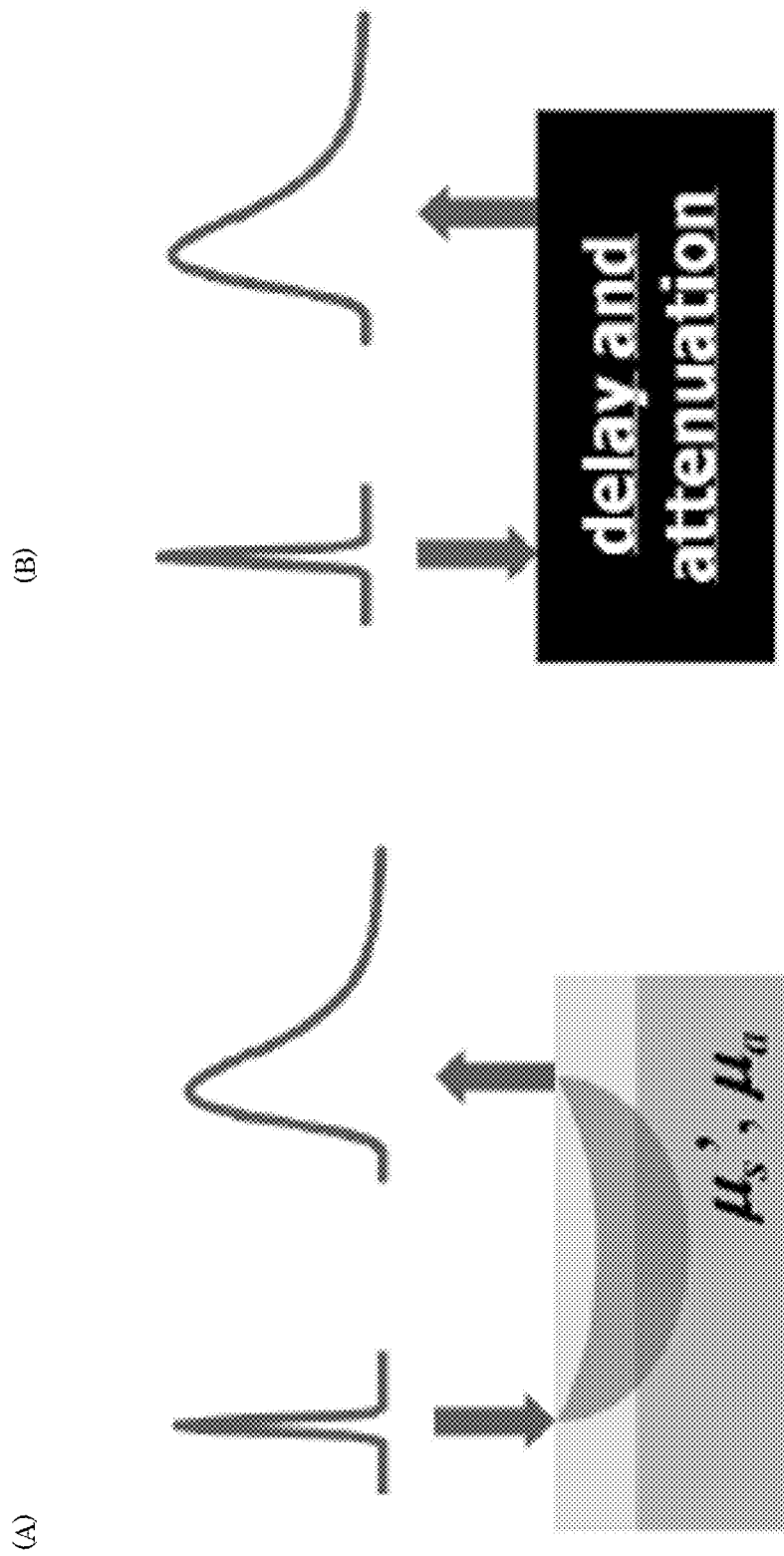
FIG. 14 shows a physical phantom in panel (a) and an optical phantom in panel (b) that produces a selected TOFD for phantom light.
Figure 15:
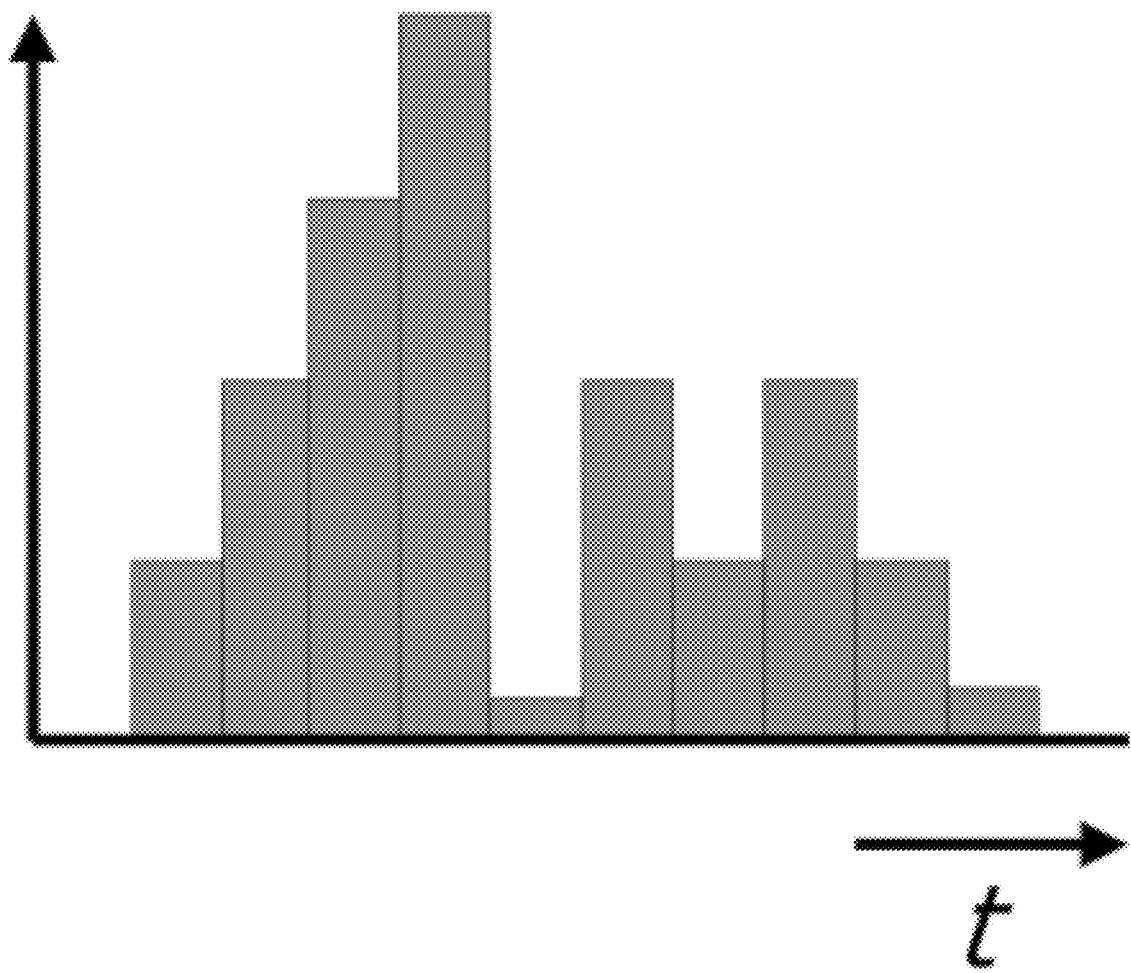
FIG. 15 shows an arbitrary waveform.
Figure 16:
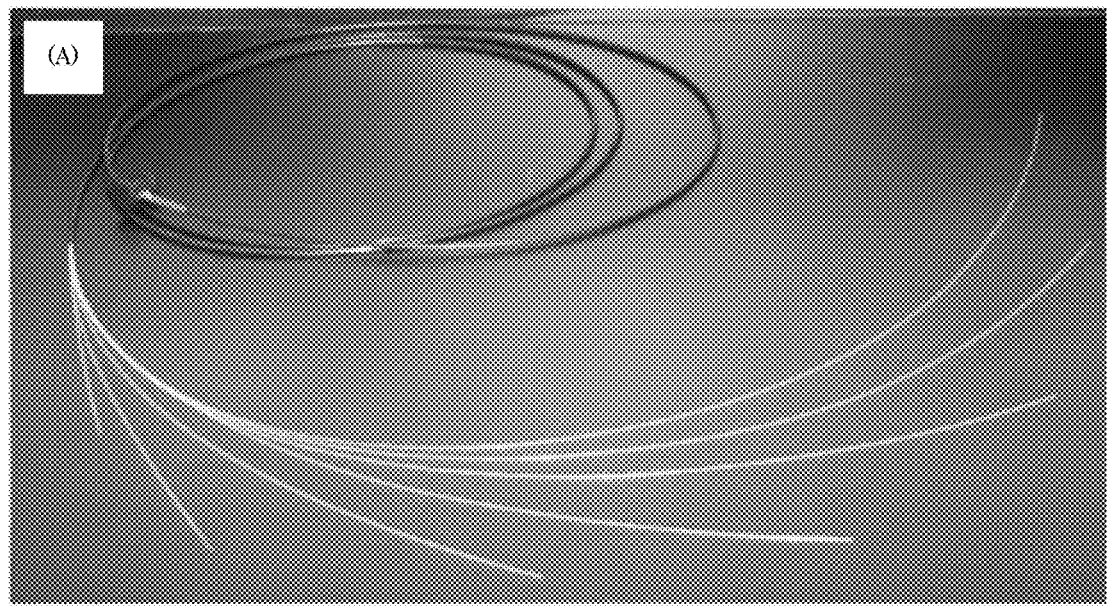
FIG. 16 shows optical delay fibers of different optical path length in panel A and that provide different delayed DTOFs in panel B.
Figure 16:
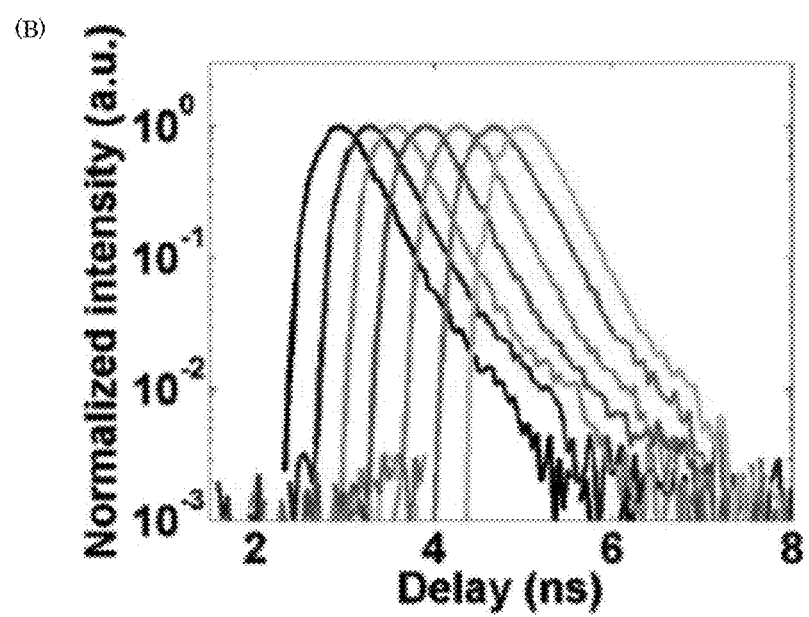

Operation of a digital phantom, in particular for cerebral oximetry, shown in panel A of FIG. 14, wherein a TOFD is produced by diffusive light propagation through a turbid medium, e.g. with two different layers, wherein each layer has a reduced scattering coefficient μs' and an absorption coefficient μa. The digital phantom produces a desired TOFD by modifying an amplitude of delayed replicas of the input pulse. The input comes from the source part of the instrument under test, and the output of the digital phantom is fed into a detection part of the instrument such that previously measured or synthetic (e.g., by mathematical simulations of light propagation) DTOFs can be provided to the device under test.

In an embodiment, with regard to light supply lines 32, probe light 12 from source optode of measuring device 26 is coupled to a light supply line 32 of spatial light modulator 214 that can have, e.g., 100 filter elements, with high and equivalent efficiency achieved by using, together with appropriate transfer lenses, a bundle of optical fibers of equal length that can have a circular shape on the input side and a linear shape on the output side. The optical fibers or free-space optics can be used here.

With regard to filter device 34, filter device 34 can be a programmable liquid-crystal spatial light modulator (SLM) such as a liquid crystal on silicon (LCoS) that changes transmittance or reflectance of each pixels 36 (e.g., 512×512 pixels) independently and over a dynamic range that can be of 3 orders of magnitude. Such array 218 is advantageous compared to DMDs that have a binary behavior that in which micromirrors are only in an on position or an off position.

With regard to optical delay line 230, a stepwise delay of filtered light 242 is advantageously provided by optical fibers 232. A length of optical fibers 232 can be obtained by cutting with equal steps from fiber-to-fiber and aligning each optical fiber 232 in a plane with end faces planarly flush and optionally sorted by length. The output of spatial light modulator 214 is imaged onto optical delay line 230. A step width in length provides a temporal step width to produce a selected TOFD. With a refractive index of 1.5 of optical fiber core material, a temporal step width of 20 ps corresponds to a difference in optical fiber length of 4 mm. A range of 2 ns is provided by optical fiber lengths differing by 400 mm and provided by 100 fibers.

It is contemplated that optical fibers 232 of optical delay line 230 do not introduce pulse broadening by temporal dispersion, and optical fibers 232 can be graded-index fibers. Optical output ends of optical fibers 232 can be arranged in a circular bundle for combining and imaging intermediate time-of-flight distributions 402 or phantom light 244 onto light detector 254.

Figure 1:
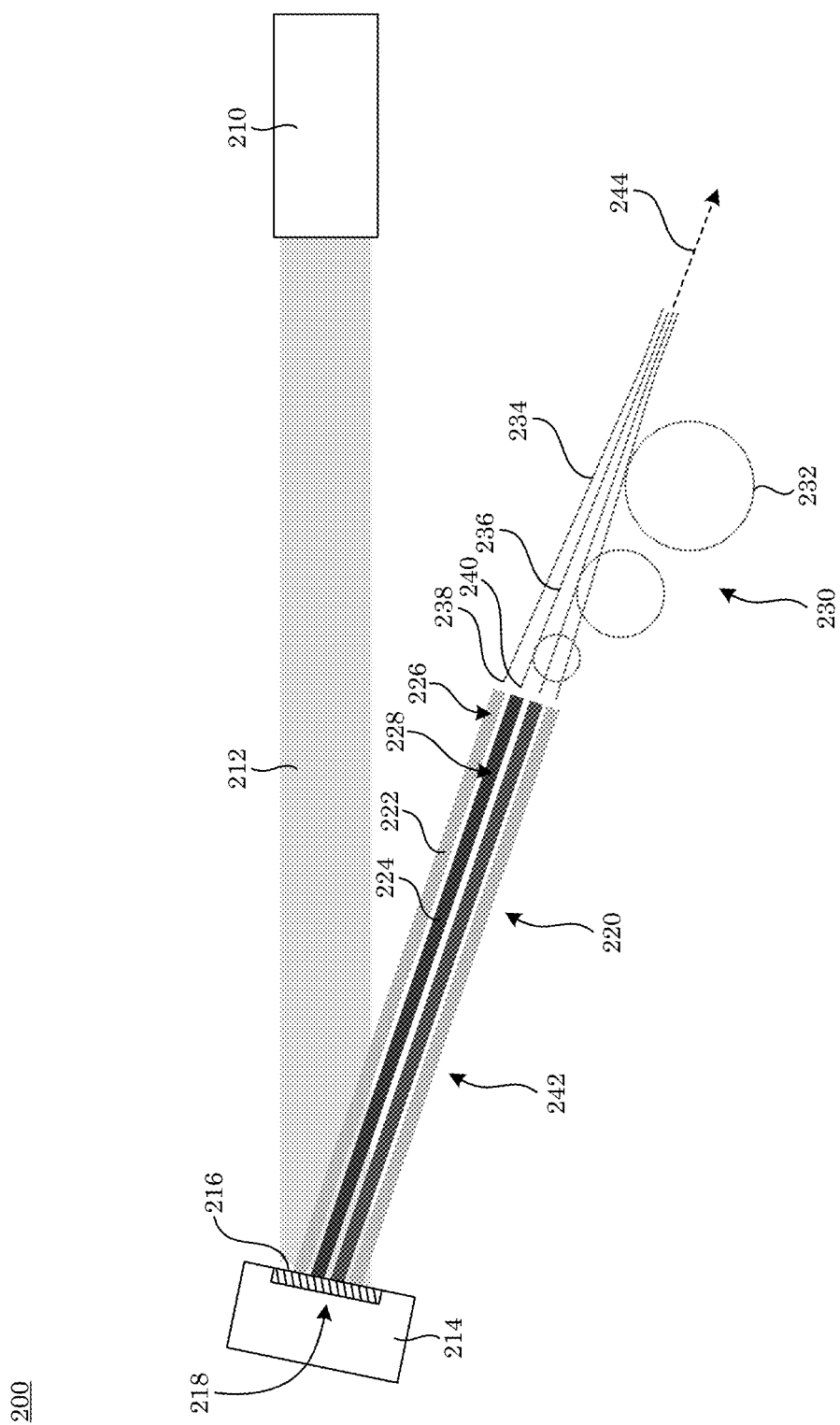
FIG. 1 shows an optical phantom.

In an embodiment, optical delay line 230 is interposed between spatial light modulator 214 and light detector 254 as shown in FIG. 1 and FIG. 13. In some embodiments, optical delay line 230 is interposed between light source 210 and spatial light modulator 214. According to an embodiment, a first optical delay line is interposed between spatial light modulator 214 and light detector 254 and a second optical delay line is interposed between light source 210 and spatial light modulator 214.

It is contemplated that a two-dimensional SLM can use one dimension to model a TOFD, and another dimension of the array to model a dependence on another parameter such as a wavelength. An imaging spectrograph can disperse first light 212 and direct communicate dispersed first light to a corresponding component of the SLM.

Optical phantom 200 mimics a delta-pulse response of a sample. When optical phantom 200 is disposed in a measurement setup instead of biological tissue 10, a finite input pulse width and final time resolution of the detection system are taken into account in the measurement. Mathematically these influences are included by a convolution similar to measurement on a real sample. Producing the optical step delay does not cause pulse broadening. A total delay caused by insertion of optical phantom 200 can be taken into account in measurement of a response function of the instrument.

Beneficially and unexpectedly, optical phantom 200 provides time-resolved measurements and mimics behavior of biological tissue 10 in a time-resolved measurement in diffuse optical imaging and spectroscopy and fluorescence decay measurements. Moreover, optical phantom 200 can be used as picosecond optical waveform synthesizer to generate selectively tailored pulses of an arbitrary shape in the ps range. Here, optical phantom 200 as an optical waveform synthesizer (also referred to as an optical waveform generator) can include a short-pulsed laser delivering, e.g., femtosecond pulses; an SLM, e.g., with a one-dimensional array; an optical delay line 230, and optional optical units therebetween to distribute and combine light. An output of optical phantom 220 can be an optical pulse (or a pulse train, for an input laser with a high repetition rate) of phantom light 244. A temporal resolution of a pulse of phantom light 244 can be modulated based on steps in fiber length, the input pulse width, dispersion effects in the fibers and optics, quality of imaging in spatial light modulator 214, and the like.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. An optical phantom to produce a time-resolved diffuse reflectance spectrum, the optical phantom comprising:
   a light source that produces a first light;
   a spatial light modulator comprising a plurality of mirrors arranged in an array, the mirrors being independently controlled to reflect the first light in a plurality of light paths comprising a first light path and a second light path, such that the spatial light modulator:
      receives the first light over the plurality of mirrors;
      selectively reflects the first light as filtered light into the light paths such that the first light path includes a first photon flux and the second light path includes a second photon flux, the first photon flux being greater than the second photon flux; and
   an optical delay line comprising a plurality of optical fibers that comprises a first delay fiber and a second delay fiber, such that:
      a first optical entrance of the first delay fiber is disposed in the first light path and receives the first photon flux from the spatial light modulator;
      a second optical entrance of the second delay fiber is disposed in the second light path and receives the second photon flux from the spatial light modulator;
      the first delay fiber has a first length and produces a first time-of-flight distribution of the first photon flux after propagating through the first delay fiber; and
      the second delay fiber has a second length and produces a second time-of-flight distribution of the second photon flux after propagating in the second delay fiber;
      the first length being different than the second length so that the first time-of-flight distribution is different than the second time-of-flight distribution; and
      a combination of the first time-of-flight distribution and the second time-of-flight distribution are combined to produce phantom light having the time-resolved diffuse reflectance spectrum.

2. The optical phantom of claim 1, further comprising a telescope interposed between the light source and the spatial light modulator, such that telescope receives the first light from the light source and enlarges a cross-sectional area of the first light to cover a selected portion of the mirrors.

3. The optical phantom of claim 1, further comprising a polarizer interposed between the light source and the spatial light modulator, such that the polarizer receives the first light from the light source and selectively polarizes the first light to be received by the mirrors.

4. The optical phantom of claim 1, further comprising a polarizer interposed between the spatial light modulator and the optical delay line, such that the polarizer receives filtered light from the spatial light modulator and selectively polarizes the filtered light to be received by the optical fibers.

5. The optical phantom of claim 1, further comprising an optical density filter interposed between the spatial light modulator and the optical delay line, such that the optical density filter:
   receives the filtered light from the spatial light modulator;
   increases a contrast between the first photon flux and the second photon flux; and
   communicates the first photon flux and the second photon flux with increased contrast to the optical delay line.

6. The optical phantom of claim 1, further comprising a light detector in optical communication with the optical delay line to receive the phantom light communicated from the optical fibers and to produce a time-of-flight signal from the first photon flux and the second photon flux.

7. The optical phantom of claim 6, further comprising a time correlator in communication with the light detector and the light source and that:
   receives the time-of-flight signal from the light detector;
   receives a timing signal from the light source; and
   correlates the first time-of-flight distribution and the second time-of-flight distribution with the timing signal from the light source.

8. An optical phantom for testing a measuring device for time-resolved diffuse optical spectroscopy, the optical phantom comprising:
   an input optic in optical communication with a light supply line;

a filter device in optical communication with the light supply line and disposed in a direction of propagation of light from light supply line; and an optical delay line in optical communication with the filter device and comprising a plurality of optical delay fibers, the optical delay fibers being arranged relative to the filter device such that light received by each of optical delay fiber is individually filtered by the filter device, the optical delay fibers being joined to receive light leaving the filter device, such that the optical delay line produces phantom light with time-resolved diffuse reflectance spectrum in response to receiving first light with an initial time-of-flight distribution at input optic, wherein optical delay fibers comprise different optical path lengths (wi) for light such that output pulse lengths of photon time-of-flight distributions from the optical delay fibers are greater than an input pulse length of the first light, and a combination of the optical delay line and the filter device provide the time-resolved diffuse reflectance spectrum that mimics a photon time-of-flight distribution produced by biological tissue upon subjecting the biological tissue to a pulse of light from the measuring device.

9. The optical phantom of claim 8, wherein the filter device comprises a spatial light modulator.

10. The optical phantom of claim 9, wherein the spatial light modulator comprises a liquid crystal light modulator.

11. The optical phantom of claim 8, wherein the optical delay fibers independently comprise a graded-index glass fiber.

12. The optical phantom of claim 8, wherein the input optic comprises a plurality of light supply lines in optical communication with the filter device such that one light supply line exists for each optical delay fiber, and light exiting the light supply line is communicated to the filter device and subsequently enters an optical delay fiber.

13. The optical phantom of claim 8, wherein the filter device comprises:

a wavelength-selective light filter; and
an array of filter elements,
wherein the filter elements are arranged such that filtering by the filter elements depends on a wavelength of light, and a plurality of different time-of-flight distributions are produced based on a difference in wavelength of light filtered by the filter device.

14. The optical phantom of claim 13, wherein the wavelength-selective light filter comprises a dispersive element.

15. A method for producing phantom light having a time-resolved diffuse reflectance spectrum for testing a measuring device for time-resolved diffuse optical spectroscopy of biological tissue, the method comprising:

illuminating a filter device with an input light pulse from an input optic, wherein each filter element of the filter device receives photons as a partial light pulse from the input light pulse incident on the filter device;

filtering the partial light pulses by the filter device, a filter transmission varies for at least one of the partial light pulses;

guiding of the partial light pulses along optical paths $w_i$ of varying lengths of an optical delay line; and merging the partial light pulses by a light collector arranged in optical communication with the filter device in a direction of light propagation, such that phantom light exits an output surface of the light collector, wherein the optical paths $w_i$ are selected and filtering is conducted such that a time-resolved diffuse reflectance spectrum of phantom light mimics a photon time-of-flight distribution produced from subjecting a biological tissue to probe light.

16. The method according to claim 15, further comprising:

producing the input light pulse by the measuring device;

collecting output photons that exit an output surface of the optical phantom;

determining a measurement value from a tissue photon time-of-flight distribution measured by the measuring device for at least two wavelengths; and comparing the measurement value with a reference value, the reference value based on the time-resolved diffuse reflectance spectrum of phantom light.

17. The method according to claim 16, wherein the measurement value is measured oxygen saturation of hemoglobin for blood in the biological tissue.

* * * * *